(12) United States Patent
Nojiri et al.

(10) Patent No.: US 12,214,061 B2
(45) Date of Patent: Feb. 4, 2025

(54) ADHESIVE COMPOSITION FOR DENTAL USE

(71) Applicant: KURARAY NORITAKE DENTAL INC., Kurashiki (JP)

(72) Inventors: Yamato Nojiri, Niigata (JP); Naoki Nishigaki, Niigata (JP); Mitsunobu Kawashima, Niigata (JP)

(73) Assignee: KURARAY NORITAKE DENTAL INC., Kurashiki (JP)

( * ) Notice: Subject to any disclaimer, the term of this patent is extended or adjusted under 35 U.S.C. 154(b) by 731 days.

(21) Appl. No.: 17/415,802

(22) PCT Filed: Dec. 20, 2019

(86) PCT No.: PCT/JP2019/050178
§ 371 (c)(1),
(2) Date: Jun. 18, 2021

(87) PCT Pub. No.: WO2020/130143
PCT Pub. Date: Jun. 25, 2020

(65) Prior Publication Data
US 2022/0071852 A1    Mar. 10, 2022

(30) Foreign Application Priority Data

Dec. 21, 2018   (JP) .................................. 2018-239568

(51) Int. Cl.
| A61K 6/30 | (2020.01) |
| A61K 6/887 | (2020.01) |
| C08F 230/02 | (2006.01) |
| C08K 5/521 | (2006.01) |

(52) U.S. Cl.
CPC ................ *A61K 6/30* (2020.01); *A61K 6/887* (2020.01); *C08F 230/02* (2013.01); *C08K 5/521* (2013.01)

(58) Field of Classification Search
None
See application file for complete search history.

(56) References Cited

U.S. PATENT DOCUMENTS 4,719,297 A * 1/1988 Henne ..................... C07F 9/36
987/153
5,055,497 A * 10/1991 Okada ................. A61L 24/0089
524/202

FOREIGN PATENT DOCUMENTS

| EP | 0 009 348 B1 | 4/1980 |
| JP | 57-197289 A | 12/1982 |
| JP | 2-28204 A | 1/1990 |
| JP | 2005-179283 A | 7/2005 |
| JP | 2006-45179 A | 2/2006 |
| JP | 2006-298771 A | 11/2006 |
| JP | 2009-191154 A | 8/2009 |
| JP | 2012-131717 A | 7/2012 |
| JP | 2013-193962 A | 9/2013 |
| JP | 2015-67551 A | 4/2015 |

OTHER PUBLICATIONS

Effects of storage temperature on the shelf life of one step and two step self etch adhesives (Year: 2009).*
Third Party Observations issued on Jun. 21, 2023 in European Patent Application No. 19900592.7, 13 pages.
Sakamoto, T., et al., "Chemistry of Dental Adhesives", Journal of the Adhesion Society of Japan, vol. 52, No. 5, pp. [152](32)-[165](45), 2016 (with partial English translation).
Sadaaki, M., et al., "Bonding Durablilty of Commercially-available Luting Systems for Ceramic Restoration to Dental Zirconia", The Journal of the Japan Prosthodontic Society, vol. 51, No. 4, pp. 733-740, 2007 (with English abstract).
Extended European Search Report issued Aug. 19, 2022 in European Patent Application No. 19900592.7, 33 pages.

(Continued)

*Primary Examiner* — Peter A Salamon
(74) *Attorney, Agent, or Firm* — Oblon, McClelland, Maier & Neustadt, L.L.P.

(57) ABSTRACT

A dental adhesive composition may exhibit high bond strength, e.g., initial bond strength and bond durability, to sandblasted zirconia. Such a dental adhesive composition may include (A) a dihydrogen phosphate monoester group-containing polymerizable monomer of formula (1):

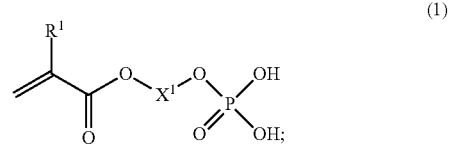

and
(B) a dihydrogen phosphate monoester group-containing compound of formula (2):

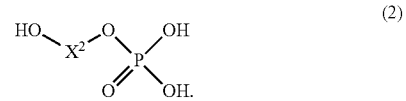

$R^1$ may be H or a methyl group, and $X^1$ and $X^2$ may be an optionally substituted, linear or branched hydrocarbon group having 8 to 16 carbon atoms. The hydrocarbon group of $X^1$ and/or $X^2$ may have a hydrocarbon chain comprising an —O—, —S—, and/or a phenylene group.

20 Claims, No Drawings

(56) References Cited

OTHER PUBLICATIONS

Third Party Observations issued Jun. 27, 2023, (Client received Jul. 18, 2023) in corresponding Japanese Patent Application No. 2020-561549 (with English Translation), 22 pages.
Written Opposition client obtained May 2, 2024, in corresponding Japanese Patent No. 7356456 (with English Translation), 130 pages.
"Study of anomeric equilibria of ketoses in water by natural-abundance carbon-13 Fourier transform nuclear magnetic resonance, D-fructose and D-turanose", Journal of American Chemical Society, 1971, 3 pages.
David J, Wilbur et al., "Detection of the Furanose Anomers of D-Mannose in Aqueous Solution. Application of Carbon-13 Nuclear Magnetic Resonance Spectroscopy at 68 MHz", Journal of American Chemical Society, 1977, 3 pages (5450-5452).
Third Party Observations issued Sep. 3, 2024 (client received Sep. 6, 2024) in corresponding European Patent Application No. 19900592.7 (12 pages).
Third Party Observations issued Sep. 10, 2024 (client received Sep. 12, 2024) in corresponding European Patent Application No. 19900592.7 (13 pages).
International Search Report issued Mar. 17, 2020 in PCT/JP2019/050178, 2 pages.
Third Party Observation, submitted on Mar. 29, 2021, PCT/JP2019/050178 (with English translation), 15 pages.
Third Party Observation, submitted on Apr. 20, 2021, PCT/JP2019/050178 (with English translation), 8 pages.
Third Party Observation, submitted on Apr. 20, 2021, PCT/JP2019/050178 (with English translation), 10 pages.
Ma, S., et al., "Effects of Storage Temperature on the Shelf Life of One-step and Two-step Self-etch Adhesives", Operative Dentistry, vol. 34, No. 4, pp. 472-480, 2009.
"Quantitative analysis of specific compounds in product" (with English translation), Uploaded literature #2—Submitted with third-party information (on Mar. 29, 2021 (Mar. 29, 2021), Report No. NS20120118, 7 pages.
CLEARFIL Universal Bond Quick ER, Kuraray America, Inc., Uploaded literature #3—Submitted with third-party information (on Mar. 29, 2021 (Mar. 29, 2021), 6 pages (with English translation).
Hosaka, K., et al., "The Influence of a Touch-cure System on the Micro-tensile Bond Strength of Self-etch Adhesives to Root Canal Dentin", The Japanese Journal of Conservative Dentistry, vol. 62, No. 1, pp. 39-46, 2019, (with English abstract).
Sakamoto, T., et al., "Chemistry of Dental Adhesives", Journal of the Adhesion Society of Japan, vol. 52, No. 5, pages [152](32)-[165](45), 2016 (with partial English translation).
Sadaaki, M., et al., "Bonding Durability of Commercially-available Luting Systems for Ceramic Restoration to Dental Zirconia", The Journal of the Japan Prosthodontic Society, vol. 51, No. 4, pp. 733-740, 2007 (with English abstract).

\* cited by examiner

ADHESIVE COMPOSITION FOR DENTAL USE

CROSS-REFERENCE TO RELATED APPLICATIONS

The present application is the national stage of international application PCT/JP2019/050178, filed on Dec. 20, 2019, and claims the benefit of the filing date of Japanese Appl. No. 2018-239568, filed on Dec. 21, 2018.

TECHNICAL FIELD

The present invention relates to a dental adhesive composition used in the field of dentistry.

BACKGROUND ART

In dentistry, a technique of bonding a crown restoration material to the tooth structure using a dental adhesive is employed for the purpose of restoration of carious teeth and chipped teeth. As crown restoration materials, metal oxide ceramics such as zirconia and alumina are used in recent years in addition to, for example, conventionally used dental metals and dental porcelains. Among the metal oxide ceramics, zirconia, in particular, is becoming increasingly widespread in clinical practice because of its excellent mechanical strength and, for example, recent development of a zirconia material having high translucency and high aesthetic quality.

When a crown restoration material made of zirconia is bonded to the tooth structure, an operation in which an adherend surface of the zirconia is sandblasted to form small asperities on the zirconia surface is commonly performed before application of a dental adhesive so as to improve bond strength. It is known that because this sandblasting applies a large mechanical energy to the zirconia surface, a portion of crystals of the zirconia undergoes a tetragonal-to-monoclinic phase transition.

Meanwhile, adhesive compositions comprising an acidic group-containing polymerizable monomer are commonly used as dental adhesives for metal oxide ceramics such as zirconia and alumina. The acidic group-containing polymerizable monomer is a polymerizable monomer having an acidic group that forms a chemical bond with a metal oxide and is selected from, for example, a phosphate group, a thiophosphate group, a phosphonate group, and a carboxylic acid group. The acidic group-containing polymerizable monomer is frequently used in dental adhesives.

For example, Patent Literature 1 proposes an adhesive material for zirconia molded bodies, the adhesive material having relatively high bond durability for sandblasted zirconia owing to a carboxylic acid group-containing polymerizable monomer in which a carboxylic acid group is bonded to a (meth)acryloyloxy or (meth)acryloylamino group via an aliphatic hydrocarbon group having a chain length of 7 to 20 carbon atoms. However, in Patent Literature 1, the bond durability is evaluated by measurement of bond strength after a relatively short thermal cycling test. According to studies by the present inventors, the adhesive material for zirconia molded bodies has insufficient longer-term bond durability and has a problem in that adhesive property thereof is decreased by a bond durability test performed assuming long-term use in a harsh environment of the oral cavity.

Moreover, Patent Literature 2 states that a multi-part dental curable composition comprising a first part comprising an acidic group-containing polymerizable monomer, a peroxy ester, and a copper compound and a second part comprising an aromatic sulfinic acid salt has high adhesive property and high bond durability for zirconia. However, in Patent Literature 2, the adhesive property was evaluated for zirconia grounded with #1000 paper, which is tetragonal zirconia. According to studies by the present inventors, long-term bond durability for sandblasted zirconia, which is zirconia including a monoclinic crystal, is insufficient and needs to be improved.

Furthermore, Non Patent Literature 1 states that a certain commercially-available adhesion system comprising an acidic group-containing polymerizable monomer exhibits high adhesive property for sandblasted zirconia. However, the adhesive property is significantly decreased by a thermal cycling test performed assuming an environment of the oral cavity, and long-term bond durability needs to be improved.

CITATION LIST

Patent Literature

Patent Literature 1: JP 2009-191154 A
Patent Literature 2: JP 2012-131717 A

Non Patent Literature

Non Patent Literature 1: S. Murahara, et al, The Journal of the Japan Prosthodontic Society, 51 (4), 733-740

SUMMARY OF INVENTION

Technical Problem

Therefore, the present invention aims to provide a dental adhesive composition that exhibits high bond strength (initial bond strength and bond durability) to sandblasted zirconia.

Solution to Problem

As a result of intensive studies, the present inventors found that the foregoing issues can be solved with the use of a specific phosphoric acid group-containing polymerizable monomer and a specific phosphoric acid group-containing compound in combination. Through further studies on the basis of this finding, the present inventors have completed the present invention.

Specifically, the present invention includes the following.
[1] A dental adhesive composition comprising:
  a dihydrogen phosphate monoester group-containing polymerizable monomer (A) represented by a general formula (1); and
  a dihydrogen phosphate monoester group-containing compound (B) represented by a general formula (2),

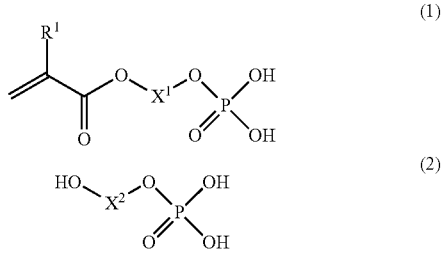

where $R^1$ represents a hydrogen atom or a methyl group and $X^1$ and $X^2$ each independently represent an optionally substituted, linear or branched hydrocarbon group having 8 to 16 carbon atoms, wherein the hydrocarbon group may have a hydrocarbon chain with one or more groups selected from the group consisting of an oxy group (—O—), a sulfide group (—S—), and a phenylene group.

[2] The dental adhesive composition according to [1], comprising a polymerizable monomer (C) that is copolymerizable with the dihydrogen phosphate monoester group-containing polymerizable monomer (A).

[3] The dental adhesive composition according to [1] or [2], further comprising a polymerization initiator (D).

[4] The dental adhesive composition according to any one of [1] to [3], wherein $X^1$ in the general formula (1) and $X^2$ in the general formula (2) are the same.

[5] The dental adhesive composition according to any one of [1] to [4], wherein the content of the dihydrogen phosphate monoester group-containing compound (B) is 0.05 to 5.0 parts by mass relative to 100 parts by mass of the dihydrogen phosphate monoester group-containing polymerizable monomer (A).

[6] The dental adhesive composition according to any one of [1] to [5], wherein $X^1$ and $X^2$ are each independently an unsubstituted, linear alkylene group having 8 to 16 carbon atoms.

[7] The dental adhesive composition according to any one of [1] to [6], comprising a polymerizable monomer (C) that is copolymerizable with the dihydrogen phosphate monoester group-containing polymerizable monomer (A), wherein
  the polymerizable monomer (C) comprises a hydrophobic polymerizable monomer (C-1) having no acidic group.

Advantageous Effects of Invention

The present invention provides a dental adhesive composition that exhibits high bond strength (initial bond strength and bond durability) to sandblasted zirconia.

DESCRIPTION OF EMBODIMENTS

A dental adhesive composition of the present invention comprises: a dihydrogen phosphate monoester group-containing polymerizable monomer (A) represented by a general formula (1); and a dihydrogen phosphate monoester group-containing compound (B) represented by a general formula (2),

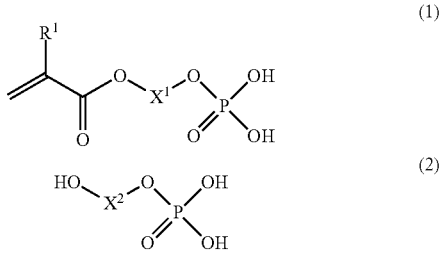

where $R^1$ represents a hydrogen atom or a methyl group and $X^1$ and $X^2$ each independently represent an optionally substituted, linear or branched hydrocarbon group having 8 to 16 carbon atoms, wherein the hydrocarbon group may have a hydrocarbon chain with one or more groups selected from the group consisting of an oxy group (—O—), a sulfide group (—S—), and a phenylene group.

The term "(meth)acryl" as used in the present specification collectively refers to methacryl and acryl. The same applies to similar expressions. In the present specification, the upper limits and lower limits of numeric ranges (for example, ranges of contents of components, ranges of values calculated from components, and numeric ranges of physical properties) can be combined appropriately.

Though the reason why the dental adhesive composition of the present invention comprising the dihydrogen phosphate monoester group-containing polymerizable monomer (A) and the dihydrogen phosphate monoester group-containing compound (B) exhibits high bond strength (initial bond strength and bond durability) to sandblasted zirconia remains unclear, a possible explanation is as follows. It has been known that a dental adhesive composition comprising the dihydrogen phosphate monoester group-containing polymerizable monomer (A) of the present invention exhibits high bond strength (initial bond strength and bond durability) to the tooth structure because a dihydrogen phosphate monoester group forms a chemical bond to the tooth structure and long-chain molecules are arranged in a regular manner by hydrophobic interaction and van der Waals interaction. It is thought that for zirconia in which a portion of crystals has undergone a tetragonal-to-monoclinic phase transition by sandblasting, the long-chain molecules arranged in a regular manner are too closely spaced on the sandblasted zirconia surface and that results in a decrease in polymerization reaction efficiency and further a decrease in bond durability. It is thought that in the present invention, because of the use of the dihydrogen phosphate monoester group-containing compound (B) in combination with the dihydrogen phosphate monoester group-containing polymerizable monomer (A), the dihydrogen phosphate monoester group-containing compound (B) are properly arranged between the dihydrogen phosphate monoester group-containing polymerizable monomers (A). Consequently, the dihydrogen phosphate monoester group-containing polymerizable monomers (A) are arranged not too closely on a sandblasted zirconia surface, and that allows efficient progress of a polymerization reaction. That is thought to be the reason for the high bond durability.

Components comprised in the dental adhesive composition of the present invention will be described hereinafter.

[Dihydrogen Phosphate Monoester Group-Containing Polymerizable Monomer (A)]

The dihydrogen phosphate monoester group-containing polymerizable monomer (A) forms a chemical bond with sandblasted zirconia, is polymerizable, and also imparts a curing effect. When used in combination with the dihydrogen phosphate monoester group-containing compound (B), the dihydrogen phosphate monoester group-containing polymerizable monomer (A), which has a long carbon chain, is arranged on a sandblasted zirconia surface in a regular manner. As a result, not only high initial bond strength but also high bond durability is exhibited for sandblasted zirconia.

The dihydrogen phosphate monoester group-containing polymerizable monomer (A) is represented by the following general formula (1).

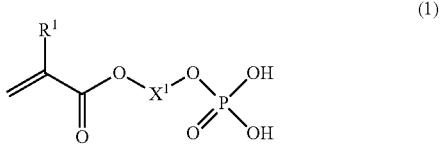

In the formula, $R^1$ represents a hydrogen atom or a methyl group, and $X^1$ represents an optionally substituted, linear or branched hydrocarbon group having 8 to 16 carbon atoms. $X^1$ may be an unsubstituted, linear alkylene group having 8 to 16 carbon atoms.

Examples of the C8 to C16 hydrocarbon group represented by $X^1$ include saturated hydrocarbon groups and unsaturated hydrocarbon groups. Examples of the C8 to C16 saturated hydrocarbon groups include C8 to C16 alkylene groups. Examples of the unsaturated hydrocarbon groups include C8 to C16 alkenylene groups. The alkylene groups may be linear or branched. Examples of the alkylene groups include an n-octylene group, a 2-ethylhexylene group, an isooctylene group, an n-nonylene group, an n-decylene group, an isodecylene group, an n-decylene group, an n-undecylene group, an isoundecylene group, an n-dodecylene group, an isododecylene group, an n-tridecylene group, an n-tetradecylene group, an n-pentadecylene group, and an n-hexadecylene group. The alkenylene groups may be linear or branched. Examples of the alkenylene groups include an n-octenylene group, an n-nonenylene group, an n-decenylene group, an n-undecenylene group, an n-dodecenylene group, an n-tridecenylene group, an n-tetradecenylene group, an n-pentadecenylene group, and an n-hexadecenylene group. The hydrocarbon group having an alkylene group or an alkenylene group may have a hydrocarbon chain with one or more groups selected from the group consisting of an oxy group (—O—), a sulfide group (—S—), and a phenylene group, or a hydrocarbon chain with one or more groups selected from the group consisting of an oxy group (—O—) and a phenylene group. Examples of the substituent include a halogen atom (fluorine, chlorine, bromine, or iodine atom), a carboxy group, a hydroxy group, an amino group, an amino group mono- or di-substituted by a C1 to C8 alkyl group, an acyl group, an acyloxy group, an amide group, a C2 to C8 alkoxycarbonyl group, a C1 to C8 alkoxy group, and a C1 to C8 alkylthio group, and a halogen atom is preferred. The number of substituents is not particularly limited. The number of substituents can be about 1 to 8, and is preferably 1 to 3. The number of carbon atoms in the hydrocarbon group for $X^1$ is preferably 8 to 15, more preferably 8 to 14, and even more preferably 8 to 12.

Known compounds can be used as the dihydrogen phosphate monoester group-containing polymerizable monomer (A) without particular limitation as long as the effect of the present invention can be obtained. In view of storage stability, compounds having a methacryloyl group (that is, $R^1$ in the general formula (1) is a methyl group) are particularly useful.

Specific examples of the dihydrogen phosphate monoester group-containing polymerizable monomer (A) include 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 13-(meth)acryloyloxytridecyl dihydrogen phosphate, 14-(meth)acryloyloxytetradecyl dihydrogen phosphate, 15-(meth)acryloyloxypentadecyl dihydrogen phosphate, and 16-(meth)acryloyloxyhexadecyl dihydrogen phosphate.

In view of adhesive property for sandblasted zirconia, 10-methacryloyloxydecyl dihydrogen phosphate is most preferred among these dihydrogen phosphate monoester group-containing polymerizable monomers (A).

The dihydrogen phosphate monoester group-containing polymerizable monomer (A) may be used alone, or two or more thereof may be used in combination. Excessively high and low contents of the dihydrogen phosphate monoester group-containing polymerizable monomer (A) may result in decrease of adhesive property. In this regard, the content of the dihydrogen phosphate monoester group-containing polymerizable monomer (A) is preferably 1 to 100 parts by mass, more preferably 2 to 70 parts by mass, even more preferably 3 to 50 parts by mass relative to total 100 parts by mass of the polymerizable monomer components in the dental adhesive composition.

[Dihydrogen Phosphate Monoester Group-Containing Compound (B)]

The dihydrogen phosphate monoester group-containing compound (B) forms a chemical bond with zirconia. The dihydrogen phosphate monoester group-containing compound (B) has a long carbon chain similar to the one the dihydrogen phosphate monoester group-containing polymerizable monomer (A) has, and a hydroxyl group at a terminal forms a hydrogen bond with an oxygen atom comprised in a (meth)acryloyloxy group of the dihydrogen phosphate monoester group-containing polymerizable monomer (A). It is inferred that because of these facts, the dihydrogen phosphate monoester group-containing compound (B) is properly arranged between the dihydrogen phosphate monoester group-containing polymerizable monomers (A) on a sandblasted zirconia surface. As a result, not only high initial bond strength but also high bond durability is exhibited for sandblasted zirconia.

The dihydrogen phosphate monoester group-containing compound (B) is represented by the following general formula (2).

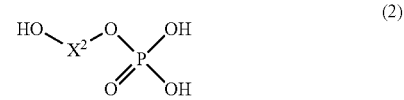

(2)

In the formula, $X^2$ represents an optionally substituted, linear or branched hydrocarbon group having 8 to 16 carbon atoms. $X^2$ may be an unsubstituted, linear alkylene group having 8 to 16 carbon atoms. Examples of the C8 to C16 hydrocarbon group represented by $X^2$ include saturated hydrocarbon groups and unsaturated hydrocarbon groups. Examples of the C8 to C16 saturated hydrocarbon groups include C8 to C16 alkylene groups. Examples of the unsaturated hydrocarbon groups include C8 to C16 alkenylene groups. The alkylene and alkenylene groups for $X^2$ are the same as the alkylene and alkenylene groups for $X^1$. The number of carbon atoms in the hydrocarbon group for $X^2$ is preferably 8 to 15, more preferably 8 to 14, and even more preferably 8 to 12.

Known compounds can be used as the dihydrogen phosphate monoester group-containing compound (B) without particular limitation as long as the effect of the present invention can be obtained. It is particularly preferred that the hydrocarbon groups of the dihydrogen phosphate monoester group-containing compound (B) and the dihydrogen phosphate monoester group-containing polymerizable monomer (A) have the same structure ($X^1$ in the general formula (1) and $X^2$ in the general formula (2) are the same) because, in that case, the dihydrogen phosphate monoester group-containing compound (B) can be arranged in a regular manner between the dihydrogen phosphate monoester group-containing polymerizable monomers (A) and the bond durability is also excellent.

Specific examples of the dihydrogen phosphate monoester group-containing compound (B) include 8-hydroxyoctyl dihydrogen phosphate, 9-hydroxynonyl dihydrogen phosphate, 10-hydroxydecyl dihydrogen phosphate, 11-hydroxyundecyl dihydrogen phosphate, 12-hydroxydodecyl dihydrogen phosphate, and 16-hydroxyhexadecyl dihydrogen phosphate.

Among these compounds, 10-hydroxydecyl dihydrogen phosphate is most preferred in view of adhesive property for sandblasted zirconia.

The dihydrogen phosphate monoester group-containing compound (B) may be used alone, or two or more thereof may be used in combination. The content of the dihydrogen phosphate monoester group-containing compound (B) is not particularly limited as long as the effect of the present invention can be obtained. However, in view of adhesive property, polymerizability, curability, and other properties of the dental adhesive composition obtained, the content of the dihydrogen phosphate monoester group-containing compound (B) is preferably 0.05 to 5.0 parts by mass, more preferably 0.1 to 3.0 parts by mass, even more preferably 0.2 to 1.0 parts by mass relative to 100 parts by mass of the dihydrogen phosphate monoester group-containing polymerizable monomer (A). If the content of the dihydrogen phosphate monoester group-containing compound (B) is less than 0.05 parts by mass, the bond durability for sandblasted zirconia may decrease. If the content of the dihydrogen phosphate monoester group-containing compound (B) is more than 5.0 parts by mass, the curability of the composition and the bond strength to sandblasted zirconia may decrease.

The method for producing the dihydrogen phosphate monoester group-containing compound (B) is not particularly limited. For example, the dihydrogen phosphate monoester group-containing compound (B) can be easily obtained by causing a reaction between alkylenediol and phosphorus oxychloride in the presence of an amine compound. Alternatively, the dihydrogen phosphate monoester group-containing compound (B) can be obtained in the form of a mixture with the dihydrogen phosphate monoester group-containing polymerizable monomer (A) as a by-product of synthesis of the dihydrogen phosphate monoester group-containing polymerizable monomer (A), and the dihydrogen phosphate monoester group-containing compound (B) and the dihydrogen phosphate monoester group-containing polymerizable monomer (A) are optionally separated. The desired dental adhesive composition can be obtained by mixing, to a desired content ratio, the dihydrogen phosphate monoester group-containing polymerizable monomer (A) and the dihydrogen phosphate monoester group-containing compound (B) separated from each other.

[Polymerizable Monomer (C)]

In view of adhesive property and mechanical strength, a dental adhesive composition of the present invention preferably comprises a polymerizable monomer (C) (hereinafter, also referred to simply as "polymerizable monomer (C)") that is copolymerizable with the dihydrogen phosphate monoester group-containing polymerizable monomer (A). A known polymerizable monomer can be used as the polymerizable monomer (C). Examples of the polymerizable monomer (C) include a hydrophobic polymerizable monomer (C-1) having no acidic group and a hydrophilic polymerizable monomer (C-2) having no acidic group. The polymerizable monomer (C) preferably comprises the hydrophobic polymerizable monomer (C-1) having no acidic group in view of the mechanical strength, ease of handling, and other properties of a cured product. The polymerizable monomer (C) may be used alone, or two or more thereof may be used in combination. For example, the hydrophobic polymerizable monomer (C-1) having no acidic group and the hydrophilic polymerizable monomer (C-2) having no acidic group may be used in combination. The polymerizable monomer (C) of the present invention comprises no polymerizable monomers that fall under the dihydrogen phosphate monoester group-containing polymerizable monomer (A).

(i) Hydrophobic Polymerizable Monomer (C-1) Having No Acidic Group

When the dental adhesive composition of the present invention comprises the hydrophobic polymerizable monomer (C-1) having no acidic group, the mechanical strength, ease of handling, and other properties of a cured product (a product resulting from curing of the dental adhesive composition) can be improved. Preferred as the hydrophobic polymerizable monomer (C-1) having no acidic group are radical polymerizable monomers having no acidic group but having a polymerizable group. For advantages such as ease of radical polymerization, the polymerizable group is preferably a (meth)acryloyl group or a (meth)acrylamide group. The hydrophobic polymerizable monomer (C-1) having no acidic group can be one having a solubility of less than 10 mass % in water at 25° C. Examples of such hydrophobic polymerizable monomers (C-1) having no acidic group include crosslinkable polymerizable monomers such as monofunctional polymerizable monomers, aromatic bifunctional monomers, aliphatic bifunctional monomers, and tri- and higher-functional monomers.

Examples of the monofunctional polymerizable monomers include 4-hydroxybutyl (meth)acrylate, 6-hydroxyhexyl (meth)acrylate, 8-hydroxyoctyl (meth)acrylate, 10-hydroxydecyl (meth)acrylate, and octafluoropentyl (meth)acrylate.

Examples of the aromatic bifunctional monomers include
2,2-bis((meth)acryloyloxyphenyl)propane,
2,2-bis[4-(3-(meth)acryloyloxy-2-hydroxypropoxy)phenyl]propane,
2,2-bis(4-(meth)acryloyloxyethoxyphenyl)propane,
2,2-bis(4-(meth)acryloyloxypolyethoxyphenyl)propane,
2,2-bis(4-(meth)acryloyloxydiethoxyphenyl)propane,
2,2-bis(4-(meth)acryloyloxytriethoxyphenyl)propane,
2,2-bis(4-(meth)acryloyloxytetraethoxyphenyl)propane,
2,2-bis(4-(meth)acryloyloxypentaethoxyphenyl)propane,
2,2-bis(4-(meth)acryloyloxydipropoxyphenyl)propane,
2-(4-(meth)acryloyloxydiethoxyphenyl)-2-(4-(meth)acryloyloxyethoxyphenyl)propane,
2-(4-(meth)acryloyloxydiethoxyphenyl)-2-(4-(meth)acryloyloxytriethoxyphenyl)propane,
2-(4-(meth)acryloyloxydipropoxyphenyl)-2-(4-(meth)acryloyloxytriethoxyphenyl)propane, 2,2-bis(4-(meth)acryloyloxypropoxyphenyl)propane, and
2,2-bis(4-(meth)acryloyloxyisopropoxyphenyl)propane.
Preferred among these are
2,2-bis[4-(3-methacryloyloxy-2-hydroxypropoxy)phenyl]propane,
2,2-bis(4-(meth)acryloyloxyethoxyphenyl)propane,
2,2-bis(4-methacryloyloxypolyethoxyphenyl)propane (a compound in which the average number of moles of ethoxy group added is 2.6),
2,2-bis(4-(meth)acryloyloxydiethoxyphenyl)propane,
2,2-bis(4-(meth)acryloyloxytriethoxyphenyl)propane,
2,2-bis(4-(meth)acryloyloxytetraethoxyphenyl)propane, and
2,2-bis(4-(meth)acryloyloxypentaethoxyphenyl)propane, and more preferred are 2,2-bis[4-(3-methacryloyloxy-2-hydroxypropoxy)phenyl]
propane and
2,2-bis(4-methacryloyloxypolyethoxyphenyl)propane (a compound in which the average number of moles of ethoxy group added is 2.6).

Examples of the aliphatic bifunctional monomers include glycerol di(meth)acrylate, ethylene glycol di(meth)acrylate, diethylene glycol di(meth)acrylate, triethylene glycol di(meth)acrylate, propylene glycol di(meth)acrylate, butylene glycol di(meth)acrylate, neopentyl glycol di(meth)acrylate, 1,3-butanediol di(meth)acrylate, 1,5-pentanediol di(meth)acrylate, 1,6-hexanediol di(meth)acrylate, 1,10-decanediol di(meth)acrylate, 1,2-bis(3-methacryloyloxy-2-hydroxypropoxy)ethane, 2,2,4-trimethylhexamethylene bis(2-carbamoyloxyethyl) di(meth)acrylate, N-methacryloyloxyethylacrylamide, N-methacryloyloxypropylacrylamide, N-methacryloyloxybutylacrylamide, N-(1-ethyl-(2-methacryloyloxy)ethyl)acrylamide, and N-(2-(2-methacryloyloxyethoxy)ethyl)acrylamide. Preferred among these are glycerol di(meth)acrylate, triethylene glycol di(meth)acrylate, neopentyl glycol di(meth)acrylate, 1,6-hexanediol di(meth)acrylate, 1,10-decanediol di(meth)acrylate, 1,2-bis(3-methacryloyloxy-2-hydroxypropoxy)ethane, 2,2,4-trimethylhexamethylene bis(2-carbamoyloxyethyl) di(meth)acrylate, N-methacryloyloxyethylacrylamide, and N-methacryloyloxypropylacrylamide.

Examples of the tri- and higher-functional monomers include trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, dipentaerythritol penta(meth)acrylate, N,N-(2,2,4-trimethylhexamethylene)bis[2-(aminocarboxy)propane-1,3-diol]tetra(meth)acrylate, and 1,7-diacryloyloxy-2,2,6,6-tetra(meth)acryloyloxymethyl-4-oxyheptane. Preferred among these is N,N-(2,2,4-trimethylhexamethylene)bis[2-(aminocarboxy)propane-1,3-diol]tetramethacrylate.

Among the above hydrophobic polymerizable monomers (C-1) having no acidic group, the aromatic bifunctional monomers and the aliphatic bifunctional monomers are preferred in view of the mechanical strength and ease of handling of a cured product. In view of bond strength, and the mechanical strength of a cured product, 2,2-bis[4-(3-methacryloyloxy-2-hydroxypropoxy)phenyl]propane, 2,2-bis(4-methacryloyloxypolyethoxyphenyl)propane (a compound in which the average number of moles of ethoxy group added is 2.6), triethylene glycol dimethacrylate, 2,2,4-trimethylhexamethylene bis(2-carbamoyloxyethyl)dimethacrylate, and N-methacryloyloxyethylacrylamide are more preferred, and 2,2-bis[4-(3-methacryloyloxy-2-hydroxypropoxy)phenyl]propane, triethylene glycol dimethacrylate, 2,2,4-trimethylhexamethylene bis(2-carbamoyloxyethyl)dimethacrylate, and N-methacryloyloxyethylacrylamide are even more preferred. The hydrophobic polymerizable monomer (C-1) having no acidic group may be used alone, or two or more thereof may be used in combination.

In view of advantages such as improvement of bond strength, the content of the hydrophobic polymerizable monomer (C-1) having no acidic group in a dental adhesive composition of the present invention is preferably at least 9 parts by mass, more preferably at least 15 parts by mass, even more preferably at least 20 parts by mass, particularly preferably at least 30 parts by mass relative to total 100 parts by mass of the polymerizable monomer components contained in the dental adhesive composition. In view of advantages such as improvement of bond strength through improved penetrability into the tooth structure, the content of the hydrophobic polymerizable monomer (C-1) having no acidic group is preferably at most 90 parts by mass, more preferably at most 80 parts by mass, even more preferably at most 75 parts by mass, particularly preferably at most 70 parts by mass relative to total 100 parts by mass of the polymerizable monomer components contained in the dental adhesive composition.

(ii) Hydrophilic Polymerizable Monomer (C-2) Having no Acidic Group

One embodiment of the present invention is a dental adhesive composition comprising the hydrophilic polymerizable monomer (C-2) having no acidic group. When the dental adhesive composition of the present invention is applied to the tooth structure, the hydrophilic polymerizable monomer (C-2) having no acidic group comprised in the dental adhesive composition allows the components of the dental adhesive composition to penetrate the tooth structure in an accelerated fashion and the hydrophilic polymerizable monomer (C-2) having no acidic group itself can also penetrate into the tooth structure and bind to the organic components (such as collagen) in the tooth structure. The hydrophilic polymerizable monomer (C-2) having no acidic group is preferably a radical polymerizable monomer having no acidic group but having a polymerizable group. For advantages such as ease of radical polymerization, the polymerizable group is preferably a (meth)acryloyl group or a (meth)acrylamide group. The hydrophilic polymerizable monomer (C-2) having no acidic group can be one having a solubility of 10 mass % or more in water at 25° C., and is preferably one having a solubility of 30 mass % or more in water at 25° C., more preferably one freely soluble in water at 25° C.

Preferred as the hydrophilic polymerizable monomer (C-2) having no acidic group are those having a hydrophilic group such as a hydroxyl group, an oxymethylene group, an oxyethylene group, an oxypropylene group, or an amide group. Examples of such hydrophilic polymerizable monomers (C-2) having no acidic group include:

(meth)acrylates such as 2-hydroxyethyl(meth)acrylate, 3-hydroxypropyl(meth)acrylate, 2-hydroxypropyl(meth)acrylate, 1,3-dihydroxypropyl(meth)acrylate, 2,3-dihydroxypropyl(meth)acrylate, 2-trimethylammonium ethyl(meth)acryl chloride, and polyethylene glycol di(meth)acrylate (having at least nine oxyethylene groups); and monofunctional (meth)acrylamides such as N-methylol(meth)acrylamide, N-hydroxyethyl(meth)acrylamide, N-methoxymethyl(meth)acrylamide, N-ethoxymethyl(meth)acrylamide, and diacetone(meth)acrylamide, 4-(meth)acryloylmorpholine, and disubstituted (meth)acrylamides represented by the following general formula (3).

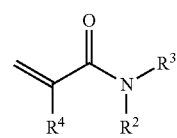

(3)

In the general formula (3), $R^2$ and W each independently represent an optionally substituted, linear or branched alkyl group having 1 to 3 carbon atoms, and $R^4$ is a hydrogen atom or a methyl group.

Examples of the C1 to C3 alkyl groups represented by $R^2$ and $R^3$ include a methyl group, an ethyl group, an n-propyl group, and an isopropyl group. Examples of the optional substituents of the alkyl group include a hydroxyl group.

Examples of the disubstituted (meth)acrylamides represented by the general formula (3) include N,N-dimethyl (meth)acrylamide, N,N-diethyl(meth)acrylamide, and N,N-di(hydroxyethyl)(meth)acrylamide. In view of, for example, storage stability, N,N-dimethylacrylamide and N,N-diethylacrylamide are preferred, and N,N-diethylacrylamide is more preferred.

Among the above hydrophilic polymerizable monomers (C-2) having no acidic group, in view of adhesive property for the tooth structure, 2-hydroxyethyl(meth)acrylate, 2,3-dihydroxypropyl(meth)acrylate, and the monofunctional (meth)acrylamides are preferred, 2-hydroxyethyl(meth)acrylate, 2,3-dihydroxypropyl(meth)acrylate, diacetone (meth)acrylamide, and the disubstituted (meth)acrylamides represented by the general formula (3) are more preferred, 2-hydroxyethyl(meth)acrylate and the disubstituted (meth)acrylamides represented by the general formula (3) are even more preferred, and 2-hydroxyethylmethacrylate and N,N-diethylacrylamide are particularly preferred. The hydrophilic polymerizable monomer (C-2) having no acidic group may be used alone, or two or more thereof may be used in combination.

In an embodiment in which the hydrophilic polymerizable monomer (C-2) having no acidic group is comprised, in view of advantages such as improvement of bond strength through improved penetrability into the tooth structure, the content of the hydrophilic polymerizable monomer (C-2) having no acidic group in a dental adhesive composition of the present invention is preferably at least 9 parts by mass, more preferably at least 15 parts by mass, even more preferably at least 20 parts by mass, particularly preferably at least 30 parts by mass relative to total 100 parts by mass of the polymerizable monomer components. In view of advantages such as improvement of bond strength, the content of the hydrophilic polymerizable monomer (C-2) having no acidic group is preferably at most 90 parts by mass, more preferably at most 80 parts by mass, even more preferably at most 75 parts by mass, particularly preferably at most 70 parts by mass relative to total 100 parts by mass of the polymerizable monomer components.

For advantages such as further improvement of adhesive property for both sandblasted zirconia and the tooth structure, the total content of all the polymerizable monomers contained in a dental adhesive composition of the present invention is preferably at least 20 parts by mass, more preferably at least 35 parts by mass, and is preferably at most 90 parts by mass, more preferably at most 80 parts by mass, relative to total 100 parts by mass of the dental adhesive composition.

A dental adhesive composition of the present invention can comprise an acidic group-containing polymerizable monomer (C-3) other than the dihydrogen phosphate monoester group-containing polymerizable monomer (A), provided that the acidic group-containing polymerizable monomer (C-3) does not interfere with the effects of the invention. Examples of the acidic group-containing polymerizable monomer (C-3) other than the dihydrogen phosphate monoester group-containing polymerizable monomer (A) include polymerizable monomers having at least one acidic group such as a phosphoric acid group, a pyrophosphoric acid group, a thiophosphoric acid group, a phosphonic acid group, a sulfonic acid group, or a carboxylic acid group, and having at least one polymerizable group such as an acryloyl group, a methacryloyl group, a vinyl group, or a styrene group. Specific examples of the acidic group-containing polymerizable monomer (C-3) other than the dihydrogen phosphate monoester group-containing polymerizable monomer (A) are as follows.

Examples of the phosphoric acid group-containing polymerizable monomer include:

dihydrogen phosphate monoester group-containing polymerizable monomers other than the dihydrogen phosphate monoester group-containing polymerizable monomer (A), such as 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, and 20-(meth)acryloyloxyicosyl dihydrogen phosphate;

hydrogen phosphate diester group-containing polymerizable monomers, such as bis[2-(meth)acryloyloxyethyl] hydrogen phosphate, bis[4-(meth)acryloyloxybutyl]hydrogen phosphate, bis[6-(meth)acryloyloxyhexyl] hydrogen phosphate, 1,3-di(meth)acryloyloxypropyl dihydrogen phosphate, 2-(meth)acryloyloxyethylphenyl hydrogen phosphate, 2-(meth)acryloyloxyethyl-2-bromoethyl hydrogen phosphate, and bis[2-(meth)acryloyloxy-(1-hydroxymethyl)ethyl]hydrogen phosphate; and acid chlorides, alkali metal salts, and ammonium salts of these.

Examples of the pyrophosphoric acid group-containing polymerizable monomer include bis[2-(meth)acryloyloxyethyl]pyrophosphate, bis[4-(meth)acryloyloxybutyl]pyrophosphate, bis[6-(meth)acryloyloxyhexyl]pyrophosphate, bis[8-(meth)acryloyloxyoctyl]pyrophosphate, bis[10-(meth)acryloyloxydecyl]pyrophosphate, and acid chlorides, alkali metal salts, and ammonium salts of these.

Examples of the thiophosphoric acid group-containing polymerizable monomer include 2-(meth)acryloyloxyethyl dihydrogen thiophosphate, 3-(meth)acryloyloxypropyl dihydrogen thiophosphate, 4-(meth)acryloyloxybutyl dihydrogen thiophosphate, 5-(meth)acryloyloxypentyl dihydrogen thiophosphate, 6-(meth)acryloyloxyhexyl dihydrogen thiophosphate, 7-(meth)acryloyloxyheptyl dihydrogen thiophosphate, 8-(meth)acryloyloxyoctyl dihydrogen thiophosphate, 9-(meth)acryloyloxynonyl dihydrogen thiophosphate, 10-(meth)acryloyloxydecyl dihydrogen thiophosphate, 11-(meth)acryloyloxyundecyl dihydrogen thiophosphate, 12-(meth)acryloyloxydodecyl dihydrogen thiophosphate, 16-(meth)acryloyloxyhexadecyl dihydrogen thiophosphate, 20-(meth)acryloyloxyicosyl dihydrogen thiophosphate, and acid chlorides, alkali metal salts, and ammonium salts of these.

Examples of the phosphonic acid group-containing polymerizable monomer include 2-(meth)acryloyloxyethylphenylphosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexylphosphonoacetate, 10-(meth)acryloyloxydecylphosphonoacetate, and acid chlorides, alkali metal salts, and ammonium salts of these.

Examples of the sulfonic acid group-containing polymerizable monomer include 2-(meth)acrylamide-2-methylpropanesulfonic acid, styrenesulfonic acid, and 2-sulfoethyl (meth)acrylate.

Examples of the carboxylic acid group-containing polymerizable monomer include polymerizable monomers having one carboxy group within the molecule and polymerizable monomers having a plurality of carboxy groups within the molecule.

Examples of the polymerizable monomers having one carboxy group within the molecule include (meth)acrylic acid, N-(meth)acryloylglycine, N-(meth)acryloylaspartic acid, O-(meth)acryloyltyrosine, N-(meth)acryloyltyrosine, N-(meth)acryloylphenylalanine, N-(meth)acryloyl-p-aminobenzoic acid, N-(meth)acryloyl-o-aminobenzoic acid, p-vinylbenzoic acid, 2-(meth)acryloyloxybenzoic acid, 3-(meth)acryloyloxybenzoic acid, 4-(meth)acryloyloxybenzoic acid, N-(meth)acryloyl-5-aminosalicylic acid, N-(meth)acryloyl-4-aminosalicylic acid, 2-(meth)acryloyloxyethyl hydrogen succinate, 2-(meth)acryloyloxyethyl hydrogen phthalate, 2-(meth)acryloyloxyethyl hydrogen malate, and acid halides of these.

Examples of the polymerizable monomers having a plurality of carboxy groups within the molecule include 6-(meth)acryloyloxyhexane-1,1-dicarboxylic acid, 9-(meth)acryloyloxynonane-1,1-dicarboxylic acid, 10-(meth)acryloyloxydecane-1,1-dicarboxylic acid, 11-(meth)acryloyloxyundecane-1,1-dicarboxylic acid, 12-(meth)acryloyloxydodecane-1,1-dicarboxylic acid, 13-(meth)acryloyloxytridecane-1,1-dicarboxylic acid, 4-(meth)acryloyloxyethyl trimellitate, 4-(meth)acryloyloxybutyl trimellitate, 4-(meth)acryloyloxyhexyl trimellitate, 4-(meth)acryloyloxydecyl trimellitate, 2-(meth)acryloyloxyethyl-3'-(meth)acryloyloxy-2'-(3,4-dicarboxybenzoyloxy)propyl succinate, and acid anhydrides or acid halides of these.

[Polymerization Initiator (D)]

In view of adhesive property, it is preferable that a dental adhesive composition of the present invention further comprise a polymerization initiator (D). A known polymerization initiator can be used as the polymerization initiator (D). For example, a photopolymerization initiator (D-1) and a chemical polymerization initiator (D-2) can be used. The polymerization initiator (D) may be used alone, or two or more thereof may be used in combination. For example, the photopolymerization initiator (D-1) and the chemical polymerization initiator (D-2) may be used in combination.

(i) Photopolymerization Initiator (D-1)

Examples of the photopolymerization initiator (D-1) include (bis)acylphosphine oxides (including salts thereof), thioxanthones (including salts such as quaternary ammonium salts), ketals, α-diketones, coumarins, anthraquinones, benzoin alkyl ethers, and α-aminoketone compounds.

Examples of the (bis)acylphosphine oxides include acylphosphine oxides, such as 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, benzoyl di(2,6-dimethylphenyl)phosphonate, and salts of these (for example, sodium salts, potassium salts, ammonium salts of these).

Examples of the (bis)acylphosphine oxides include bisacylphosphine oxides, such as bis(2,6-dichlorobenzoyl)phenylphosphine oxide, bis(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoyl)phenylphosphine oxide, bis(2,6-dimethoxybenzoyl)-2,4,4-trimethylpentylphosphine oxide, bis(2,6-dimethoxybenzoyl)-2,5-dimethylphenylphosphine oxide, bis(2,4,6-trimethylbenzoyl)phenylphosphine oxide, bis(2,3,6-trimethylbenzoyl)-2,4,4-trimethylpentylphosphine oxide, and salts of these (for example, sodium salts, potassium salts, ammonium salts of these).

The acylphosphine oxides may be water-soluble acylphosphine oxides. Examples of the water-soluble acylphosphine oxides include those having ions, such as alkali metal ions, alkaline earth metal ions, pyridinium ions, and ammonium ions, within the acylphosphine oxide molecule. The water-soluble acylphosphine oxides can be synthesized using, for example, the methods disclosed in EP 0009348 B1 and JP 57(1982)-197289 A.

Specific examples of the water-soluble acylphosphine oxides include monomethyl acetylphosphonate·sodium salt, monomethyl(1-oxopropyl)phosphonate·sodium salt, monomethyl benzoylphosphonate·sodium salt, monomethyl (1-oxobutyl)phosphonate·sodium salt, monomethyl(2-methyl-1-oxopropyl)phosphonate·sodium salt, acetylphosphonate·sodium salt, methyl 4-(hydroxymethoxyphosphinyl)-4-oxobutanoate·sodium salt, methyl 4-oxo-4-phosphonobutanoate-monosodium salt, acetylphenylphosphinate-sodium salt, (1-oxopropyl)pentylphosphinate·sodium salt, methyl 4-(hydroxypentylphosphinyl)-4-oxobutanoate·sodium salt, acetylpentylphosphinate·sodium salt, acetylethylphosphinate·sodium salt, methyl 4-(hydroxymethylphosphinyl)-4-oxobutanoate·lithium salt, 4-(hydroxymethylphosphinyl)-4-oxobutanoic acid·dilithium salt, acetylphosphinate·sodium salt, acetylmethylphosphinate oxime·sodium salt, acetylmethylphosphinate-o-benzyloxime·sodium salt, acetylmethylphosphinate semicarbazone·sodium salt, formylmethyl phosphinate·sodium salt, methyl(1-oxopropyl)phosphinate·sodium salt, acetylmethylphosphinate thiosemicarbazone·sodium salt, sodium salts of 2,4,6-trimethylbenzoylphenylphosphine oxide, potassium salts of 2,4,6-trimethylbenzoylphenylphosphine oxide, and ammonium salts of 2,4,6-trimethylbenzoylphenylphosphine oxide.

Particularly preferred among these (bis)acylphosphine oxides are 2,4,6-trimethylbenzoyldiphenylphosphine oxide, 2,4,6-trimethylbenzoylmethoxyphenylphosphine oxide, bis (2,4,6-trimethylbenzoyl)phenylphosphine oxide, and sodium salts of 2,4,6-trimethylbenzoylphenylphosphine oxide.

Examples of the thioxanthones include thioxanthone, 2-chlorothioxanthen-9-one,
2-hydroxy-3-(9-oxo-9H-thioxanthen-4-yloxy)-N,N,N-trimethylpropaneaminium chloride,
2-hydroxy-3-(1-methyl-9-oxo-9H-thioxanthen-4-yloxy)-N,N,N-trimethyl-1-propaneaminium chloride,
2-hydroxy-3-(9-oxo-9H-thioxanthen-2-yloxy)-N,N,N-trimethyl-1-propaneaminium chloride,
2-hydroxy-3-(3,4-dimethyl-9-oxo-9H-thioxanthen-2-yloxy)-N,N,N-trimethyl-1-propaneaminium chloride,
2-hydroxy-3-(3,4-dimethyl-9H-thioxanthen-2-yloxy)-N,N,N-trimethyl-1-propaneaminium chloride, and
2-hydroxy-3-(1,3,4-trimethyl-9-oxo-9H-thioxanthen-2-yloxy)-N,N,N-trimethyl-1-propaneaminium chloride.

Preferred among these thioxanthones are 2-chlorothioxanthen-9-one and 2-hydroxy-3-(3,4-dimethyl-9H-thioxanthen-2-yloxy)-N,N,N-trimethyl-1-propaneaminium chloride.

Examples of the ketals include benzyl dimethyl ketal and benzyl diethyl ketal.

Examples of the α-diketones include diacetyl, benzyl, DL-camphorquinone, 2,3-pentadione, 2,3-octadione, 9,10-phenanthrenequinone, 4,4'-oxybenzyl, and acenaphthenequinone. Particularly preferred is DL-camphorquinone for its maximum absorption wavelength occurring in the visible light region.

Examples of the coumarins include 3,3'-carbonyl bis(7-diethylaminocoumarin), 3-(4-methoxybenzoyl)coumarin, 3-thienylcoumarin, 3-benzoyl-5,7-dimethoxycoumarin, 3-benzoyl-7-methoxycoumarin, 3-benzoyl-6-methoxycoumarin, 3-benzoyl-8-methoxycoumarin, 3-benzoylcoumarin, 7-methoxy-3-(p-nitrobenzoyl)coumarin, 3-(p-nitrobenzoyl)coumarin, 3,5-carbonyl bis(7-methoxycoumarin), 3-benzoyl-6-bromocoumarin, 3,3'-carbonyl-bis-coumarin, 3-benzoyl-7-dimethylaminocoumarin, 3-benzoylbenzo[f]coumarin, 3-carboxycoumarin, 3-carboxy-7-methoxycoumarin, 3-ethoxycarbonyl-6-methoxycoumarin, 3-ethoxycarbonyl-8-methoxycoumarin, 3-acetylbenzo[f]coumarin, 3-benzoyl-6-nitrocoumarin, 3-benzoyl-7-diethylaminocoumarin, 7-dimethylamino-3-(4-methoxybenzoyl)coumarin, 7-diethylamino-3-(4-methoxybenzoyl)coumarin, 7-diethylamino-3-(4-diethylamino)coumarin, 7-methoxy-3-(4-methoxybenzoyl)coumarin, 3-(4-nitrobenzoyl)benzo[f]coumarin, 3-(4-ethoxycinnamoyl)-7-methoxycoumarin, 3-(4-dimethylaminocinnamoyl)coumarin, 3-(4-diphenylaminocinnamoyl)coumarin, 3-[(3-dimethylbenzothiazol-2-ylidene)acetyl]coumarin, 3-[(1-methylnaphtho[1,2-D]thiazol-2-ylidene)acetyl]coumarin, 3,3'-carbonyl bis(6-methoxycoumarin), 3,3'-carbonyl bis(7-acetoxycoumarin), 3,3'-carbonyl bis(7-dimethylaminocoumarin), 3-(2-benzothiazolyl)-7-(diethylamino)coumarin, 3-(2-benzothiazolyl)-7-(dibutylamino)coumarin, 3-(2-benzoimidazolyl)-7-(diethylamino)coumarin, 3-(2-benzothiazolyl)-7-(dioctylamino)coumarin, 3-acetyl-7-(dimethylamino)coumarin, 3,3'-carbonyl bis(7-dibutylaminocoumarin), 3,3'-carbonyl-7-diethylaminocoumarin-7'-bis(butoxyethyl)aminocoumarin, 10-[3-[4-(dimethylamino)phenyl]-1-oxo-2-propenyl]-2,3,6,7-tetrahydro-1,1,7,7-tetramethyl-1H,5H,11H-[1]benzopyrano[6,7,8-ij]quinolizin-11-one, and 10-(2-benzothiazolyl)-2,3,6,7-tetrahydro-1,1,7,7-tetramethyl-1H,5H,11H-[1]benzopyrano[6,7,8-ij]quinolizin-11-one.

Preferred among these coumarins are 3,3'-carbonyl bis(7-diethylaminocoumarin) and 3,3'-carbonyl bis(7-dibutylaminocoumarin).

Examples of the anthraquinones include anthraquinone, 1-chloroanthraquinone, 2-chloroanthraquinone, 1-bromoanthraquinone, 1,2-benzanthraquinone, 1-methylanthraquinone, 2-ethylanthraquinone, and 1-hydroxyanthraquinone.

Examples of the benzoin alkyl ethers include benzoin methyl ether, benzoin ethyl ether, benzoin isopropyl ether, and benzoin isobutyl ether.

Examples of the α-aminoketone compounds include 2-methyl-1-[4-(methylthio)phenyl]-2-morpholinopropan-1-one.

Preferred among these photopolymerization initiators (D-1) is at least one selected from the group consisting of the (bis)acylphosphine oxides, the α-diketones, and the coumarins. In that case, a dental adhesive composition is provided that has desirable photocurability in both the visible light region and the near ultraviolet region, and that shows sufficient photocurability regardless of whether the light source used is a halogen lamp, a light emitting diode (LED), or a xenon lamp.

(ii) Chemical Polymerization Initiator (D-2)

A known chemical polymerization initiator can be used as the chemical polymerization initiator (D-2). Specific examples of the chemical polymerization initiator (D-2) include organic peroxides and inorganic peroxides.

Examples of the organic peroxides include ketone peroxides, hydroperoxides, diacyl peroxides, dialkyl peroxides, peroxyketals, peroxyesters, and peroxydicarbonates. Among these, hydroperoxides and peroxyesters are particularly preferred and peroxyesters are most preferred for an overall balance of safety, storage stability, and radical generating potential.

Examples of the ketone peroxides include methyl ethyl ketone peroxide, methyl isobutyl ketone peroxide, methylcyclohexanone peroxide, and cyclohexanone peroxide.

Examples of the hydroperoxides include 2,5-dimethylhexane-2,5-dihydroperoxide, diisopropylbenzene hydroperoxide, cumene hydroperoxide, t-butyl hydroperoxide, and 1,1,3,3-tetramethylbutyl hydroperoxide.

Examples of the diacyl peroxides include acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide.

Examples of the dialkyl peroxides include di-t-butyl peroxide, dicumyl peroxide, t-butylcumyl peroxide, 2,5-dimethyl-2,5-di(t-butylperoxy)hexane, 1,3-bis(t-butylperoxyisopropyl)benzene, and 2,5-dimethyl-2,5-di(t-butylperoxy)-3-hexyne.

Examples of the peroxyketals include 1,1-bis(t-butylperoxy)-3,3,5-trimethylcyclohexane, 1,1-bis(t-butylperoxy)cyclohexane, 2,2-bis(t-butylperoxy)butane, 2,2-bis(t-butylperoxy)octane, and n-butyl 4,4-bis(t-butylperoxy)valerate.

Examples of the peroxyesters include α-cumylperoxy neodecanoate, t-butylperoxy neodecanoate, t-butyl peroxypivalate, 2,2,4-trimethylpentylperoxy-2-ethylhexanoate, t-amylperoxy-2-ethylhexanoate, t-butyl peroxy-2-ethylhexanoate, di-t-butyl peroxyisophthalate, di-t-butyl peroxyhexahydroterephthalate, t-butyl peroxy-3,3,5-trimethylhexanoate, t-butyl peroxyacetate, t-butyl peroxybenzoate, and t-butyl peroxyvalerate.

Examples of the peroxydicarbonates include di-3-methoxybutyl peroxydicarbonate, di(2-ethylhexyl)peroxydicarbonate, bis(4-t-butylcyclohexyl)peroxydicarbonate, diisopropyl peroxydicarbonate, di-n-propyl peroxydicarbonate, di(2-ethoxyethyl)peroxydicarbonate, and diallyl peroxydicarbonate.

Examples of the inorganic peroxides include peroxydisulfates and peroxydiphosphates. Among these, peroxydisulfates are preferred in view of curability. Specific examples of the peroxydisulfates include sodium peroxydisulfate, potassium peroxydisulfate, aluminum peroxydisulfate, and ammonium peroxydisulfate.

In view of the bond strength and other properties of the dental adhesive composition obtained, the content of the polymerization initiator (D) in a dental adhesive composition of the present invention is preferably at least 0.01 parts by mass, more preferably at least 0.05 parts by mass, even more preferably at least 0.1 parts by mass relative to total 100 parts by mass of the polymerizable monomer components. In view of the bond strength and other properties of the dental adhesive composition obtained, the content of the polymerization initiator (D) is preferably at most 10 parts by mass relative to total 100 parts by mass of the polymerizable monomer components.

[Polymerization Accelerator (E)]

The dental adhesive composition of the present invention can further comprise a polymerization accelerator CE). Preferably, the polymerization accelerator (E) is used with the polymerization initiator (D). A known polymerization accelerator can be used as the polymerization accelerator (E). Examples of the polymerization accelerator (E) include amines, sulfinic acids (including salts), borate compounds, derivatives of barbituric acid, triazine compounds, copper compounds, tin compounds, vanadium compounds, halogen compounds, aldehydes, thiol compounds, sulfites, bisulfites, and thiourea compounds. The polymerization accelerator (E) may be used alone, or two or more thereof may be used in combination.

The amines can be classified into aliphatic amines and aromatic amines. Examples of the aliphatic amines include: primary aliphatic amines such as n-butylamine, n-hexylamine, and n-octylamine; secondary aliphatic amine such as diisopropylamine, dibutylamine, and N-methylethanolamine; and tertiary aliphatic amines such as N-methyldiethanolamine, N-ethyldiethanolamine, N-n-butyldiethanolamine, N-lauryldiethanolamine, 2-(dimethylamino) ethylmethacrylate, N-methyldiethanolaminedimethacrylate, N-ethyldiethanolaminedimethacrylate, triethanolaminemonomethacrylate, triethanolaminedimethacrylate, triethanolaminetrimethacrylate, triethanolamine, trimethylamine, triethylamine, and tributylamine. In view of the adhesive property and storage stability of the dental adhesive composition, preferred among these are tertiary aliphatic amines, and more preferred are N-methyldiethanolamine and triethanolamine.

Examples of the aromatic amines include N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-diisopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, ethyl 4-(N,N-dimethylamino)benzoate, methyl 4-(N,N-dimethylamino)benzoate, propyl 4-(N,N-dimethylamino)benzoate, n-butoxyethyl 4-(N,N-dimethylamino)benzoate, 2-[(meth)acryloyloxy]ethyl 4-(N,N-dimethylamino)benzoate, 4-(N,N-dimethylamino)benzophenone, butyl 4-dimethylaminobenzoate, and 4-(dimethylamino)benzonitrile. In view of the ability to impart excellent adhesive property to the dental adhesive composition, preferred among these are N,N-di(2-hydroxyethyl)-p-toluidine, ethyl 4-(N,N-dimethylamino) benzoate, n-butoxyethyl 4-(N,N-dimethylamino)benzoate, and 4-(N,N-dimethylamino)benzophenone.

Examples of the sulfinic acids include p-toluenesulfinic acid, sodium p-toluenesulfnate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfinate, and calcium 2,4,6-triisopropylbenzenesulfinate. Particularly preferred among these are sodium benzenesulfinate, sodium p-toluenesulfinate, and sodium 2,4,6-triisopropylbenzenesulfnate.

The borate compounds are preferably arylborate compounds. Examples of the arylborate compounds include borate compounds having one to four aryl groups per molecule.

Examples of the borate compounds having one aryl group per molecule include trialkylphenylboron, trialkyl(p-chlorophenyl)boron, trialkyl(p-fluorophenyl)boron, trialkyl[3,5-bis(trifluoromethyl)phenyl]boron, trialkyl[3,5-bis(1,1,1,3,3,3-hexafluoro-2-methoxy-2-propyl)phenyl]boron, trialkyl(p-nitrophenyl)boron, trialkyl(m-nitrophenyl)boron, trialkyl(p-butylphenyl)boron, trialkyl(m-butylphenyl)boron, trialkyl (p-butyloxyphenyl)boron, trialkyl(m-butyloxyphenyl) boron, trialkyl(p-octyloxyphenyl)boron, trialkyl(m-octyloxyphenyl)boron (the alkyl group in these compounds is, for example, n-butyl, n-octyl, or n-dodecyl), and salts thereof (e.g., sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

Examples of the borate compounds having two aryl groups per molecule include dialkyl diphenylboron, dialkyl di(p-chlorophenyl)boron, dialkyl di(p-fluorophenyl)boron, dialkyl di[3,5-bis(trifluoromethyl)phenyl]boron, dialkyl di[3,5-bis(1,1,1,3,3,3-hexafluoro-2-methoxy-2-propyl)phenyl]boron, dialkyl di(p-nitrophenyl)boron, dialkyl di(m-nitrophenyl)boron, dialkyl di(p-butylphenyl)boron, dialkyl di(m-butylphenyl)boron, dialkyl di(p-butyloxyphenyl)boron, dialkyl di(m-butyloxyphenyl)boron, dialkyl di(p-octyloxyphenyl)boron, dialkyl di(m-octyloxyphenyl)boron (the alkyl group in these compounds is, for example, n-butyl, n-octyl, or n-dodecyl), and salts thereof (e.g., sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

Examples of the borate compounds having three aryl groups per molecule include monoalkyl triphenylboron, monoalkyl tri(p-chlorophenyl)boron, monoalkyl tri(p-fluorophenyl)boron, monoalkyl tri[3,5-bis(trifluoromethyl)phenyl]boron, monoalkyl tri[3,5-bis(1,1,1,3,3,3-hexafluoro-2-methoxy-2-propyl)phenyl]boron, monoalkyl tri(p-nitrophenyl)boron, monoalkyl tri(m-nitrophenyl)boron, monoalkyl tri(p-butylphenyl)boron, monoalkyl tri(m-butylphenyl)boron, monoalkyl tri(p-butyloxyphenyl)boron, monoalkyl tri(m-butyloxyphenyl)boron, monoalkyl tri(p-octyloxyphenyl)boron, monoalkyl tri(m-octyloxyphenyl) boron (the alkyl group in these compounds is, for example, n-butyl, n-octyl, or n-dodecyl), and salts thereof (e.g., sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

Examples of the borate compounds having four aryl groups per molecule include tetraphenylboron, tetrakis(p-chlorophenyl)boron, tetrakis(p-fluorophenyl)boron, tetrakis [3,5-bis(trifluoromethyl)phenyl]boron, tetrakis[3,5-bis(1,1,1,3,3,3-hexafluoro-2-methoxy-2-propyl)phenyl]boron, tetrakis(p-nitrophenyl)boron, tetrakis(m-nitrophenyl)boron, tetrakis(p-butylphenyl)boron, tetrakis(m-butylphenyl)boron, tetrakis(p-butyloxyphenyl)boron, tetrakis(m-butyloxyphenyl)boron, tetrakis(p-octyloxyphenyl)boron, tetrakis(m-octyloxyphenyl)boron, (p-fluorophenyl)triphenylboron,

[3,5-bis(trifluoromethyl)phenyl]triphenylboron, (p-nitrophenyl)triphenylboron, (m-butyloxyphenyl)triphenylboron, (p-butyloxyphenyl)triphenylboron, (m-octyloxyphenyl)triphenylboron, (p-octyloxyphenyl)triphenylboron, and salts thereof (e.g., sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

In view of storage stability, the borate compounds having three or four aryl groups per molecule are preferred among these borate compounds. One of the arylborate compounds may be used alone, or two or more thereof may be used in combination.

Examples of the derivatives of barbituric acid include barbituric acid, 1,3-dimethylbarbituric acid, 1,3-diphenylbarbituric acid, 1,5-dimethylbarbituric acid, 5-butylbarbituric acid, 5-ethylbarbituric acid, 5-isopropylbarbituric acid, 5-cyclohexylbarbituric acid, 1,3,5-trimethylbarbituric acid, 1,3-dimethyl-5-ethylbarbituric acid, 1,3-dimethyl-5-n-butylbarbituric acid, 1,3-dimethyl-5-isobutylbarbituric acid, 1,3-dimethyl-5-cyclopentylbarbituric acid, 1,3-dimethyl-5-cyclohexylbarbituric acid, 1,3-dimethyl-5-phenylbarbituric acid, 1-cyclohexyl-1-ethylbarbituric acid, 1-benzyl-5-phenylbarbituric acid, 5-methylbarbituric acid, 5-propylbarbituric acid, 1,5-diethylbarbituric acid, 1-ethyl-5-methylbarbituric acid, 1-ethyl-5-isobutylbarbituric acid, 1,3-diethyl-5-butylbarbituric acid, 1-cyclohexyl-5-methylbarbituric acid, 1-cyclohexyl-5-ethylbarbituric acid, 1-cyclohexyl-5-octylbarbituric acid, 1-cyclohexyl-5-hexylbarbituric acid, 5-butyl-1-cyclohexylbarbituric acid, 1-benzyl-5-phenylbarbituric acid, thiobarbituric acids, and salts thereof. Examples of the salts of the derivatives of barbituric acid include alkali metal salts and alkaline earth metal salts (including magnesium salts), more specifically, sodium 5-butylbarbiturate, sodium 1,3,5-trimethylbarbiturate, and sodium 1-cyclohexyl-5-ethylbarbiturate.

Particularly preferred derivatives of barbituric acid are 5-butylbarbituric acid, 1,3,5-trimethylbarbituric acid, 1-cyclohexyl-5-ethylbarbituric acid, 1-benzyl-5-phenylbarbituric acid, and sodium salts thereof.

Examples of the triazine compounds include 2,4,6-tris(trichloromethyl)-s-triazine, 2,4,6-tris(tribromomethyl)-s-triazine,
2-methyl-4,6-bis(trichloromethyl)-s-triazine,
2-methyl-4,6-bis(tribromomethyl)-s-triazine,
2-phenyl-4,6-bis(trichloromethyl)-s-triazine,
2-(p-methoxyphenyl)-4,6-bis(trichloromethyl)-s-triazine,
2-(p-methylthiophenyl)-4,6-bis(trichloromethyl)-s-triazine,
2-(p-chlorophenyl)-4,6-bis(trichloromethyl)-s-triazine,
2-(2,4-dichlorophenyl)-4,6-bis(trichloromethyl)-s-triazine,
2-(p-bromophenyl)-4,6-bis(trichloromethyl)-s-triazine,
2-(p-tolyl)-4,6-bis(trichloromethyl)-s-triazine,
2-n-propyl-4,6-bis(trichloromethyl)-s-triazine,
2-($\alpha,\alpha,\beta$-trichloroethyl)-4,6-bis(trichloromethyl)-s-triazine,
2-styryl-4,6-bis(trichloromethyl)-s-triazine,
2-[2-(p-methoxyphenyl)ethenyl]-4,6-bis(trichloromethyl)-s-triazine,
2-[2-(o-methoxyphenyl)ethenyl]-4,6-bis(trichloromethyl)-s-triazine,
2-[2-(p-butoxyphenyl)ethenyl]-4,6-bis(trichloromethyl)-s-triazine,
2-[2-(3,4-dimethoxyphenyl)ethenyl]-4,6-bis(trichloromethyl)-s-triazine,
2-[2-(3,4,5-trimethoxyphenyl)ethenyl]-4,6-bis(trichloromethyl)-s-triazine,
2-(1-naphthyl)-4,6-bis(trichloromethyl)-s-triazine,
2-(4-biphenylyl)-4,6-bis(trichloromethyl)-s-triazine,
2-[2-{N,N-bis(2-hydroxyethyl)amino}ethoxy]-4,6-bis(trichloromethyl)-s-triazine,
2-[2-{N-hydroxyethyl-N-ethylamino}ethoxy]-4,6-bis(trichloromethyl)-s-triazine,
2-[2-{N-hydroxyethyl-N-methylamino}ethoxy]-4,6-bis(trichloromethyl)-s-triazine,
and 2-[2-{N,N-diallylamino}ethoxy]-4,6-bis(trichloromethyl)-s-triazine.

Among these triazine compounds, 2,4,6-tris(trichloromethyl)-s-triazine is preferred in view of polymerization activity, and 2-phenyl-4,6-bis(trichloromethyl)-s-triazine, 2-(p-chlorophenyl)-4,6-bis(trichloromethyl)-s-triazine, and 2-(4-biphenylyl)-4,6-bis(trichloromethyl)-s-triazine are preferred in view of storage stability. One of the triazine compounds may be used alone, or two or more thereof may be used in combination.

Examples of the copper compounds include copper acetylacetonate, copper(II) acetate, copper oleate, copper(I) chloride, and copper(II) bromide.

Examples of the tin compounds include di-n-butyltin dimaleate, di-n-octyltin dimaleate, di-n-octyltin dilaurate, and di-n-butyltin dilaurate. Preferred among these are di-n-octyltin dilaurate and di-n-butyltin dilaurate.

The vanadium compounds are preferably vanadium compounds having a valence of IV and V. Examples of vanadium compounds having a valence of IV and V include vanadium (V) oxide, vanadium(V)oxy acetylacetonate, vanadyl oxalate, vanadyl sulfate, vanadium(IV) oxobis(1-phenyl-1,3-butanedionate), bis(maltolato)oxovanadium(V), vanadium(V) oxide, sodium metavanadate, and ammonium metavanadate.

Examples of the halogen compounds include dilauryldimethylammonium chloride, lauryldimethylbenzylammonium chloride, benzyltrimethylammonium chloride, tetramethylammonium chloride, benzyldimethylcetylammonium chloride, and dilauryldimethylammonium bromide.

Examples of the aldehydes include terephthalaldehyde and derivatives of benzaldehyde. Examples of the derivatives of benzaldehyde include dimethylaminobenzaldehyde, p-methoxybenzaldehyde, p-ethoxybenzaldehyde, and p-n-octyloxybenzaldehyde. In view of adhesive property, p-n-octyloxybenzaldehyde is preferred among these.

Examples of the thiol compounds include 3-mercaptopropyltrimethoxysilane, 2-mercaptobenzooxazole, decanethiol, and thiobenzoic acid.

Examples of the sulfites include sodium sulfite, potassium sulfite, calcium sulfite, and ammonium sulfite.

Examples of the bisulfites include sodium bisulfite and potassium bisulfite.

Examples of the thiourea compounds include 1-(2-pyridyl)-2-thiourea, thiourea, methylthiourea, ethylthiourea, N,N'-dimethylthiourea, N,N'-diethylthiourea, N,N'-di-n-propylthiourea, N,N'-dicyclohexylthiourea, trimethylthiourea, triethylthiourea, tri-n-propylthiourea, tricyclohexylthiourea, tetramethylthiourea, tetraethylthiourea, tetra-n-propylthiourea, and tetracyclohexylthiourea.

In view of the bond strength and other properties of the dental adhesive composition obtained, the content of the polymerization accelerator (E) in a dental adhesive composition of the present invention is preferably at least 0.01 parts by mass, more preferably at least 0.05 parts by mass, even more preferably at least 0.1 parts by mass relative to total 100 parts by mass of the polymerizable monomer components. In view of the bond strength and other properties of the dental adhesive composition obtained, the content of the polymerization accelerator (E) is preferably at most 10 parts by mass, more preferably at most 7 parts by mass, even more preferably at most 5 parts by mass relative to total 100 parts by mass of the polymerizable monomer components.

[Filler (F)]

In certain embodiments, the dental adhesive composition of the present invention may further comprise a filler (F). Typically, the filler (F) can be broadly classified into an organic filler, an inorganic filler, and an organic-inorganic composite filler. Examples of the material of the organic filler include polymethyl methacrylate, polyethyl methacrylate, a methyl methacrylate-ethyl methacrylate copolymer, crosslinked polymethyl methacrylate, crosslinked polyethyl methacrylate, polyamide, polyvinyl chloride, polystyrene, chloroprene rubber, nitrile rubber, an ethylene-vinyl acetate copolymer, a styrene-butadiene copolymer, an acrylonitrile-styrene copolymer, and an acrylonitrile-styrene-butadiene copolymer. One of these may be used alone, or two or more thereof can be used as a mixture. The shape of the organic filler is not particularly limited, and the particle diameter of the organic filler used can be selected as appropriate. In view of ease of handling, mechanical strength, and other properties of the dental adhesive composition obtained, the organic filler has an average particle diameter of preferably 0.001 to 50 μm, more preferably 0.001 to 10 μm.

Examples of the material of the inorganic filler include quartz, silica, alumina, silica-titania, silica-titania-barium oxide, silica-zirconia, silica-alumina, lanthanum glass, borosilicate glass, soda glass, barium glass, strontium glass, glass-ceramic, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass. One of these may be used alone, or two or more thereof can be used as a mixture. The shape of the inorganic filler is not particularly limited, and the particle diameter of the inorganic filler used can be selected as appropriate. In view of ease of handling, mechanical strength, and other properties of the dental adhesive composition obtained, the inorganic filler has an average particle diameter of preferably 0.001 to 50 μm, more preferably 0.001 to 10 μm.

Examples of the shape of the inorganic filler include an irregular shape and a spherical shape. In view of improving the mechanical strength of the composition obtained, the inorganic filler is preferably a spherical filler. Another advantage of using a spherical filler is that it can produce a composite resin having superior surface gloss when a dental adhesive composition of the present invention is used as a self-adhesive dental composite resin. Here, the spherical filler refers to a filler whose particles are rounded in shape as observed in a unit area of field of view in an electron micrograph and have an average aspect ratio of 0.6 or more calculated as an average of values determined by dividing a diameter of each particle in a direction orthogonal to the maximum diameter of the particle by the maximum diameter. The spherical filler has an average particle diameter of preferably 0.05 to 5 μm. An average particle diameter of less than 0.05 μm may result in decrease of the filling rate of the spherical filler in the dental adhesive composition, and decrease of mechanical strength. With an average particle diameter of more than 5 μm, the surface area of the spherical filler may decrease, and the dental adhesive composition may fail to produce a cured product having high mechanical strength.

In order to adjust the flowability of the dental adhesive composition, the inorganic filler may be used after an optional surface treatment with a known surface treatment agent such as a silane coupling agent. Examples of such surface treatment agents include vinyltrimethoxysilane, vinyltriethoxysilane, vinyltrichlorosilane, vinyltri(β-methoxyethoxy)silane, γ-methacryloyloxypropyltrimethoxysilane, 8-methacryloyloxyoctyltrimethoxysilane, 11-methacryloyloxyundecyltrimethoxysilane, γ-glycidoxypropyltrimethoxysilane, γ-mercaptopropyltrimethoxysilane, and γ-aminopropyltriethoxysilane.

The organic-inorganic composite filler used in the present invention is a filler prepared by pulverizing a product of polymerization of a paste-like material prepared by adding a monomer component to the inorganic filler. Examples of the organic-inorganic composite filler include a TMPT filler (a polymerized and pulverized mixture of trimethylolpropanetrimethacrylate and a silica filler). The shape of the organic-inorganic composite filler is not particularly limited, and the particle diameter of the organic-inorganic composite filler used can be selected as appropriate. In view of ease of handling, mechanical strength, and other properties of the composition obtained, the organic-inorganic composite filler has an average particle diameter of preferably 0.001 to 50 μm, more preferably 0.001 to 10 μm.

In the present specification, the average particle diameter of the filler (F) is an average primary particle diameter, and can be determined by using a laser diffraction scattering method, or by observing particles with an electron microscope. Specifically, a laser diffraction scattering method is more convenient for particles of 0.1 μm or more, whereas electron microscopy is a more convenient method of particle diameter measurement for ultrafine particles of less than 0.1 μm. Here, 0.1 μm is a measured value by a laser diffraction scattering method.

As a specific example of a laser diffraction scattering method, a laser diffraction particle size distribution analyzer (SALD-2300, manufactured by Shimadzu Corporation) can be used with a 0.2% sodium hexametaphosphate aqueous solution used as a dispersion medium.

As a specific example of electron microscopy, particles may be photographed with an electron microscope (Model S-4000, manufactured by Hitachi, Ltd.), and the size of particles (at least 200 particles) observed in a unit field of the micrograph may be measured using image-analyzing particle-size-distribution measurement software (Macview, manufactured by Mountech Co., Ltd.). Here, the particle diameter is determined as an arithmetic mean value of the maximum and minimum lengths of particles, and the average primary particle diameter is calculated from the number of particles and the particle diameter.

In the present invention, two or more types of fillers differing in material, particle size distribution, and form may be mixed or may be used in combination. Unintentional inclusion of non-filler particles as impurities is acceptable, provided that such particles are not detrimental to the effects of the present invention.

The content of the filler (F) used in the present invention is not particularly limited, and is preferably 0 to 2,000 parts by mass relative to total 100 parts by mass of the polymerizable monomer components in the dental adhesive composition. The preferred content of filler (F) largely depends on the embodiment. The preferred filler (F) contents for different embodiments will be discussed below in conjunction with the descriptions of specific embodiments of the dental adhesive composition of the present invention.

[Solvent (G)]

In certain embodiments, the dental adhesive composition of the present invention preferably comprises a solvent (G). Examples of the solvent (G) include water, organic solvents, and mixed solvents of these.

In the case where the dental adhesive composition of the present invention comprises water, 1 to 2,000 parts by mass of water is preferably comprised relative to total 100 parts by mass of the polymerizable monomer components. Preferably, water is free of adverse impurities. Preferably, water is distilled water or ion-exchange water.

Examples of the organic solvent include methanol, ethanol, 1-propanol, 2-propanol, 1-butanol, 2-methyl-2-propanol, acetone, methyl ethyl ketone, tetrahydrofuran, diethyl ether, diisopropyl ether, hexane, toluene, chloroform, ethyl acetate, and butyl acetate. Considering both safety against the body and volatility for ease of removal, the organic solvent is preferably a water-soluble organic solvent, specifically, ethanol, 2-propanol, 2-methyl-2-propanol, acetone, or tetrahydrofuran. The content of the organic solvent is not particularly limited, and, in certain embodiments, addition of the organic solvent may not be necessary. In an embodiment using the organic solvent, 1 to 2,000 parts by mass of the organic solvent is preferably comprised relative to total 100 parts by mass of the polymerizable monomer components.

[Fluorine-Ion Releasing Substance (H)]

The dental adhesive composition of the present invention may further comprise a fluorine-ion releasing substance (H). With the fluorine-ion releasing substance (H), a dental adhesive composition can be obtained that can impart acid resistance to the tooth structure. Examples of the fluorine-ion releasing substance (H) include metal fluorides such as sodium fluoride, potassium fluoride, sodium monofluorophosphate, lithium fluoride, and ytterbium fluoride. The fluorine-ion releasing substance (H) may be used alone, or two or more thereof may be used in combination.

The dental adhesive composition may additionally comprise other components such as a pH adjuster, a polymerization inhibitor, a thickener, a colorant, a fluorescent agent, and a flavor, provided that such additional components do not interfere with the effects of the present invention. The dental adhesive composition may also comprise an antimicrobial substance such as cetylpyridinium chloride, benzalkonium chloride, (meth)acryloyloxydodecylpyridinium bromide, (meth)acryloyloxyhexadecylpyridinium chloride, (meth)acryloyloxydecylammonium chloride, or triclosan. The dental adhesive composition of the present invention may also comprise a polyvalent metal compound (I) to improve bond strength. It is to be noted, however, that a dental adhesive composition of the present invention exhibits sufficient bond strength to sandblasted zirconia even in embodiments in which the polyvalent metal compound (I) is not used. Examples of the polyvalent metal compound (I) include at least one compound selected from the group consisting of a polyvalent metal alkoxide, a polyvalent metal carbonate, a polyvalent metal hydride, and an alkyl polyvalent metal. Examples of the organic group of the polyvalent metal alkoxide include methylethyl, n-propyl, isopropyl, n-butyl, isobutyl, n-pentyl, n-hexyl, cyclohexyl, n-heptyl, 2-ethylhexyl, and n-octyl. Preferred among these are alkyl groups having at most four carbon atoms. The alkyl group of the alkyl polyvalent metal is, for example, but not particularly limited to, an alkyl group having 1 to 20 carbon atoms. Polyvalent metal alkoxides are preferred among these for their ability to provide high storage stability and improved bond strength. One of these compounds may be used alone, or two or more thereof may be used in combination. A metallic element constituting the polyvalent metal compound is, for example, but not particularly limited to, the metallic elements in Groups 2 to 13 of the periodic table. Preferred for desirable bond strength are Group 4 metallic elements, particularly preferably titanium. Specific examples of the polyvalent metal carbonate include calcium carbonate, barium carbonate, aluminum carbonate, lanthanum carbonate, yttrium carbonate, zirconium carbonate, and zinc carbonate. Specific examples of the polyvalent metal hydride include calcium hydride, aluminum hydride, and zirconium hydride. Specific examples of the alkyl polyvalent metal include diethyl magnesium, and trimethyl aluminum.

A dental adhesive composition of the present invention may comprise a known dye or a known pigment.

A dental adhesive composition of the present invention can be used as, for example, a dental primer, a dental bonding material, a self-adhesive dental composite resin, a dental cement, a pit and fissure sealant, a loose tooth fixing material, or an orthodontic adhesive. A dental adhesive composition of the present invention is particularly suited as a dental primer, a dental bonding material, a self-adhesive dental composite resin, or a dental cement. For these applications, a dental adhesive composition of the present invention may be used as a two-part (two-pack or two-paste) dental adhesive composition of two separate parts. The following describes specific embodiments of different applications of the dental adhesive composition.

<Dental Primer>

A known primer comprising acidic group-containing polymerizable monomers can be used to constitute a dental primer by replacing some or all of the acidic group-containing polymerizable monomers with the dihydrogen phosphate monoester group-containing polymerizable monomer (A) and the dihydrogen phosphate monoester group-containing compound (B) of the present invention. An exemplary application of the dental adhesive composition (hereinafter, also referred to simply as "primer composition") as a dental primer is a primer composition comprising the dihydrogen phosphate monoester group-containing polymerizable monomer (A), the dihydrogen phosphate monoester group-containing compound (B), and the solvent (G). Other preferred primer compositions are a primer composition as described above that further comprises the polymerizable monomer (C) and a primer composition as described above that further comprises the polymerization initiator (D) and the polymerization accelerator (E). In another preferred example, any of the primer compositions above comprises preferably 0.1 to 100 parts by mass of a mixture of the dihydrogen phosphate monoester group-containing polymerizable monomer (A) and the dihydrogen phosphate monoester-containing compound (B) and 6 to 3500 parts by mass of the solvent (G), more preferably 0.25 to 50 parts by mass of a mixture of the dihydrogen phosphate monoester group-containing polymerizable monomer (A) and the dihydrogen phosphate monoester group-containing compound (B) and 7 to 2000 parts by mass of the solvent (G), even more preferably 0.5 to 25 parts by mass of a mixture of the dihydrogen phosphate monoester group-containing polymerizable monomer (A) and the dihydrogen phosphate monoester group-containing compound (B), 20 to 99 parts by mass of the polymerizable monomer (C), and 7 to 2000 parts by mass of the solvent (G), relative to total 100 parts by mass of the polymerizable monomer components. In another preferred example, the primer composition above comprising the polymerization initiator (D) and the polymerization accelerator (E) comprises preferably 0.001 to 30 parts by mass of the polymerization initiator (D) and 0.001 to 30 parts by mass of the polymerization accelerator (E), more preferably 0.05 to 20 parts by mass of the polymerization initiator (D) and 0.05 to 20 parts by mass of the polymerization accelerator (E), relative to total 100 parts by mass of the polymerizable monomer components. For purposes such as viscosity adjustment, any of the primer compositions above may comprise 0 to 5 parts by mass of the filler (F) relative to total 100 parts by mass of the polymerizable monomer components.

<Dental Cement>

Another preferred embodiment of the dental adhesive composition of the present invention is a dental cement. Preferred examples of the dental cement include resin cements and resin-reinforced glass ionomer cements. A self-etching primer, for example, may be used as a pretreatment agent for the dental cement. A preferred exemplary application of the dental adhesive composition (hereinafter, also referred to simply as "dental cement") as a dental cement is a composition comprising the dihydrogen phosphate monoester group-containing polymerizable monomer (A), the dihydrogen phosphate monoester group-containing compound (B), the polymerizable monomer (C), the polymerization initiator (D), the polymerization accelerator (E), and the filler (F). In another preferred example, the polymerizable monomer (C) in the dental cement above comprises the hydrophobic polymerizable monomer (C-1) having no acidic group. In another preferred example, the polymerizable monomer (C) in any of the dental cements above comprises the hydrophilic polymerizable monomer (C-2) having no acidic group. In another preferred example, the polymerization initiator (D) in any of the dental cements above comprises the chemical polymerization initiator (D-2). In another preferred example, any of the dental cements above is a dual-cure dental cement in which the polymerization initiator (D) comprises the photopolymerization initiator (D-1) and the chemical polymerization initiator (D-2). Any of the dental cements above may be a two-part (two-paste) dental cement of two separate parts. In this case, it is preferable that the first part mixed with the second part comprise the polymerization initiator (D) (for example, the chemical polymerization initiator (D-2)), and the second part mixed with the first part comprise the polymerization accelerator (E).

The dental cement comprises preferably 1 to 90 parts by mass of a mixture of the dihydrogen phosphate monoester group-containing polymerizable monomer (A) and the dihydrogen phosphate monoester group-containing compound (B) and 1 to 90 parts by mass of the polymerizable monomer (C), more preferably 5 to 80 parts by mass of a mixture of the dihydrogen phosphate monoester group-containing polymerizable monomer (A) and the dihydrogen phosphate monoester group-containing compound (B) and 5 to 80 parts by mass of the polymerizable monomer (C), relative to total 100 parts by mass of the polymerizable monomer components in the dental adhesive composition. The dental cement comprises preferably 0.001 to 30 parts by mass of the polymerization initiator (D), 0.001 to 20 parts by mass of the polymerization accelerator (E), and 51 to 2,000 parts by mass of the filler (F), more preferably 0.05 to 10 parts by mass of the polymerization initiator (D), 0.05 to 10 parts by mass of the polymerization accelerator (E), and 100 to 1,500 parts by mass of the filler (F), relative to total 100 parts by mass of the polymerizable monomer components.

The present invention encompasses embodiments obtainable by combining the above features in various manners within the technical scope of the present invention as long as the effect of the present invention can be obtained.

EXAMPLES

The following describes the present invention in greater detail by way of Examples. However, the present invention is in no way limited by the following Examples. It should also be noted that the combinations of the features discussed in the Examples below do not necessarily represent all the means necessary for solving the problems identified in the present invention. The components used in the following Examples and Comparative Examples, the abbreviations and the structures of these components, and the test methods used are presented below.

[Dihydrogen Phosphate Monoester Group-Containing Polymerizable Monomer (A)]
  MDP: 10-Methacryloyloxydecyl dihydrogen phosphate
  MOP: 8-Methacryloyloxyoctyl dihydrogen phosphate
[Dihydrogen Phosphate Monoester Group-Containing Compound (B)]
  HDP: 10-Hydroxydecyl dihydrogen phosphate
  HOP: 8-Hydroxyoctyl dihydrogen phosphate
[Polymerizable Monomer (C)]
  (i) Hydrophobic polymerizable monomer (C-1) having no acidic group
  Bis-GMA: 2,2-Bis[4-(3-methacryloyloxy-2-hydroxypropoxy)phenyl]propane
  D2.6E: 2,2-Bis(4-methacryloyloxypolyethoxyphenyl)propane (a compound in which the average number of moles of ethoxy group added is 2.6)
  3G: Triethylene glycol dimethacrylate
  MAEA: N-Methacryloyloxyethylacrylamide
  (ii) Hydrophilic polymerizable monomer (C-2) having no acidic group
  HEMA: 2-Hydroxyethyl methacrylate
  DEAA: N,N-Diethylacrylamide
[Polymerization Initiator (D)]
  (i) Photopolymerization initiator (D-1)
  CQ: DL-Camphorquinone
  BAPO: Bis(2,4,6-trimethylbenzoyl)phenylphosphine oxide
  (ii) Chemical polymerization initiator (D-2)
  BPB: t-Butyl peroxybenzoate
  BPO: Benzoyl peroxide
  KPS: Potassium peroxydisulfate
[Polymerization Accelerator (E)]
  DABE: Ethyl 4-(N,N-dimethylamino)benzoate
  DEPT: N,N-Di(2-hydroxyethy)-p-toluidine
  TPSS: Sodium 2,4,6-triisopropylbenzenesulfinate
[Filler (F)]
  Inorganic filler 1: Fine silica particle "AEROSIL (registered trademark) R 972" manufactured by Nippon Aerosil Co., Ltd.; average particle diameter: 16 nm
  Inorganic filler 2: Aluminum oxide "AEROXIDE (registered trademark) AluC" manufactured by Nippon Aerosil Co., Ltd.; average particle diameter: 13 nm
  Inorganic filler 3: Silane-treated silica stone powder
  A silica stone powder (manufactured by Nitchitsu Co., Ltd. under the trade name Hi-Silica) was pulverized with a ball mill to obtain a pulverized silica stone powder. The pulverized silica stone powder had an average particle diameter of 2.2 μm as measured with a laser diffraction particle size distribution analyzer (Model SALD-2300, manufactured by Shimadzu Corporation). The pulverized silica stone powder was surface treated with 4 parts by mass of γ-methacryloyloxypropyltrimethoxysilane relative to 100 parts by mass of the pulverized silica stone powder, using an ordinary method. This produced a silane-treated silica stone powder.

Inorganic Filler 4: Silane-Treated Barium Glass Powder

A barium glass (E-3000, manufactured by Esstech under the trade name E-3000) was pulverized with a ball mill to obtain a barium glass powder. The barium glass powder had an average particle diameter of 2.4 µm as measured with a laser diffraction particle size distribution analyzer (Model SALD-2300, manufactured by Shimadzu Corporation). The barium glass powder was surface treated with 3 parts by mass of γ-methacryloyloxypropyltrimethoxysilane relative to 100 parts by mass of the barium glass powder, using an ordinary method. This produced a silane-treated barium glass powder.

[Other]

BHT: 2,6-Di-t-butyl-4-methylphenol (stabilizer, polymerization inhibitor)

Synthesis Example 1: Synthesis of HDP

A 300 mL four-neck flask were charged with 100 mL of THF, 21.6 g (0.124 moles) of 1,10-decanediol, and 13.8 g (0.136 moles) of triethylamine in succession, and the mixture was cooled to −40° C. The solution was then stirred at −30° C. for 3 hours after dropping a 30 mL THF solution of phosphorus oxychloride (19.0 g; 0.124 moles) into the four-neck flask over a time period of 1 hour. After raising the solution temperature to room temperature, the mixture was poured into 200 mL of water, heated to 80° C., and stirred for 5 hours. The solution was then cooled to room temperature, and extracted three times with 150 mL of ethyl acetate. After being dried over magnesium sulfate, the mixture was concentrated under reduced pressure. A portion of the obtained residue was separated and refined by preparative thin-layer chromatography (hereinafter abbreviated as "PTLC") to give 1.1 g of 10-hydroxydecyl dihydrogen phosphate (HDP), which was a desired compound, in the form of a colorless oily crude product.

HDP:

$^1$H-NMR (400 MHz, CDCl$_3$): 1.17-1.78 (m, 18H), 3.51 (m, 2H), 4.71 (s, 1H)

Synthesis Example 2: Synthesis of HOP

A 300 mL four-neck flask were charged with 100 mL of THF, 18.1 g (0.124 moles) of 1,10-octanediol, and 13.8 g (0.136 moles) of triethylamine in succession, and the mixture was cooled to −40° C. The solution was then stirred at −30° C. for 3 hours after dropping a 30 mL THF solution of phosphorus oxychloride (19.0 g; 0.124 moles) into the four-neck flask over a time period of 1 hour. After raising the solution temperature to room temperature, the mixture was poured into 200 mL of water, heated to 80° C., and stirred for 5 hours. The solution was then cooled to room temperature, and extracted three times with 150 mL of ethyl acetate. After being dried over magnesium sulfate, the mixture was concentrated under reduced pressure. A portion of the obtained residue was separated and refined by PTLC to give 0.8 g of 8-hydroxyoctyl dihydrogen phosphate (HOP), which was a desired compound, in the form of a colorless oily crude product.

HOP:

$^1$H-NMR (400 MHz, CDCl$_3$): 1.15-1.76 (m, 14H), 3.51 (s, 2H), 4.68 (s, 1H)

Example 1 and Comparative Example 1:
Application of Dental Adhesive

Composition as Dental Primer

Examples 1-1 to 1-9, and Comparative Example 1-1

Dental primer compositions of Examples 1-1 to 1-9 and Comparative Example 1-1 were prepared using the foregoing components, specifically, by mixing the components of Table 1 under ordinary temperature. The dental primer compositions were then measured for tensile bond strength to sandblasted zirconia, using the methods below. Table 1 shows the proportions (parts by mass) of the components of the dental primers of Examples and Comparative Examples and the test results.

Cylindrical (12 mm in inner diameter×5 mm in height) sintered zirconia bodies (obtained by sintering at 1500° C. for 2 hours) produced from a zirconia disc (manufactured by Kuraray Noritake Dental Inc. under the trade name "Noritake KATANA (registered trademark) Zirconia" HT) for CAD/CAM systems were used as adherends. Each adherend was ground with #1000 silicon carbide paper (manufactured by Nihon Kenshi Co., Ltd.) to be flat and smooth, and was dried by removing water from the grounded surface of the adherend by air-blowing. After the drying, the dried surface was sandblasted using a 50-micron alumina abrasive (manufactured by J. Morita Corp.) to obtain a treated adherend surface.

An adhesive tape with a 5-mm-diameter hole was attached to the treated adherend surface to define the joining area. Each of the dental primer compounds of Examples and Comparative Example prepared in the above manner was applied to the hole portion. After being left for 10 seconds, the surface was dried by blowing air until the applied dental primer composition was no longer flowable. Meanwhile, one end surface (having a circular cross section) of a cylindrical stainless steel rod (7 mm in diameter and 2.5 cm in length) separately prepared was sandblasted using a 50-micron alumina abrasive (manufactured by J. Morita Corp.). A primer (manufactured by Kuraray Noritake Dental Inc. under the trade name "ALLOY PRIMER") for bonding metals was applied onto the sandblasted end surface. Then, a dental resin cement (a composition obtained by kneading "Panavia (registered trademark) V5" (trade name) (manufactured by Kuraray Noritake Dental Inc.) using a mixing tip at a volume ratio of 1:1) was placed on the treated adherend surface to which the above dental primer composition was applied. Subsequently, with the center of the circular hole being aligned with the center of the cylindrical stainless steel rod, the treated surface of the stainless steel rod treated using the above primer for bonding metals was pressed against the resin cement in such a manner that the cylindrical stainless steel rod stands perpendicular to the zirconia surface. The excess dental resin cement around the cylindrical stainless steel rod was removed with an instrument. Then, two points at the interface between the bottom surface of the stainless steel rod and the zirconia surface were each irradiated with light for 10 seconds using a dental LED photoirradiator (manufactured by J. Morita Corp. under the trade name "PenCure 2000"). The sample was left to stand at room temperature for 1 hour. After that, the sample was immersed in distilled water and left to stand for 24 hours in a thermostatic chamber maintained at 37° C. to prepare an adhesion test sample. There were produced 20 such adhesion test samples. All samples were left to stand for 24 hours in a thermostatic chamber maintained at 37° C. To evaluate initial bond strength, 10 out of the 20 samples were measured for tensile bond strength immediately after left to stand for 24 hours. To evaluate bond durability, the remaining 10 samples were further subjected to 100,000 cycles of thermal cycling, one cycle of which consists of immersion in 4° C. cold water and 60° C. hot water for 1 minute each, and then measured for tensile bond strength.

The adhesion test samples were each measured for tensile bond strength using a universal testing machine (manufactured by Shimadzu Corporation) with a crosshead speed set at 2 mm/min, and the mean value was calculated as the tensile bond strength of the sample.

take KATANA (registered trademark) Zirconia" HT) for CAD/CAM systems were used as adherends. Each adherend was ground with #1000 silicon carbide paper (manufactured by Nihon Kenshi Co., Ltd.) to be flat and smooth, and was dried by removing water from the grounded surface of the adherend by air-blowing. After the drying, the dried surface was sandblasted using a 50-micron alumina abrasive (manufactured by J. Morita Corp.) to obtain a treated adherend surface.

An adhesive tape with a 5-mm-diameter hole was attached to the treated adherend surface to define the joining area. Meanwhile, one end surface (having a circular cross section) of a cylindrical stainless steel rod (7 mm in diameter

| Components (parts by mass) | | | Ex. 1-1 | Ex. 1-2 | EX. 1-3 | Ex. 1-4 | Ex. 1-5 | Ex. 1-6 | Ex. 1-7 | Ex. 1-8 | Ex. 1-9 | Comp. Ex. 1-1 |
|---|---|---|---|---|---|---|---|---|---|---|---|---|
| Dihydrogen phosphate monoester group-containing polymerizable monomer (A) | | MDP | 1 | 1 | 1 | 1 | 10 | 0.1 | | 1 | 1 | 1 |
| | | MOP | | | | | | | 1 | | | |
| Dihydrogen phosphate monoester group-containing compound (B) | | HDP | 0.01 | 0.001 | 0.04 | 0.01 | 0.05 | 0.001 | | 0.01 | 0.01 | |
| | | HOP | | | | | | | 0.01 | | | |
| Content of (B) relative to 100 parts by mass of (A) (parts by mass) | | | 1.00 | 0.10 | 4.00 | 1.00 | 0.50 | 1.00 | 1.00 | 1.00 | 1.00 | 0.00 |
| Polymerizable monomer (C) | Hydrophobic polymerizable monomer (C-1) having no acidic group | D2.6E | | | | 5 | | | | | | |
| Polymerization initiator (D) | Photopolymerization initiator (D-1) | CQ | | | | | | | | 0.3 | 0.2 | |
| | | BAPO | | | | | | | | | 0.3 | |
| Polymerization accelerator (E) | | DABE | | | | | | | | 0.5 | 0.5 | |
| Solvent (G) | | Ethanol | 99 | 99 | 99 | 94 | 90 | 99.9 | 99 | 99 | 99 | 99 |
| Initial bond strength | Tensile bond strength after being left for 24 hours (MPa) | | 33 | 31 | 32 | 35 | 31 | 30 | 30 | 36 | 37 | 32 |
| Bond durability | Tensile bond strength after thermal cycling (MPa) | | 29 | 27 | 27 | 31 | 26 | 26 | 25 | 32 | 34 | 19 |

As shown in Table 1, the dental primers according to the present invention (Examples 1-1 to 1-9) exhibited a tensile bond strength of 30 MPa or more as initial bond strength and a tensile bond strength of 25 MPa or more as bond durability for sandblasted zirconia. In contrast, while having an initial bond strength of 30 MPa or less for zirconia, the dental primer (Comparative Example 1-1) that did not contain the dihydrogen phosphate monoester group-containing monomer (B) had a bond durability of less than 20 MPa for zirconia.

Example 2 and Comparative Example 2:
Application of Dental Adhesive Composition as Dental Cement Examples 2-1 to 2-10 and Comparative Example 2-1

Two-part dental cements of Examples 2-1 to 2-10 and Comparative Example 2-1 were prepared using the foregoing components, specifically, by mixing and kneading the components of Table 2 under ordinary temperature. The dental cements were then measured for tensile bond strength to sandblasted zirconia using the method below. Table 2 shows the proportions (parts by mass) of the components of the dental cements of Examples and Comparative Example and the test results.

Cylindrical (12 mm in inner diameter×5 mm in height) sintered zirconia bodies (obtained by sintering at 1500° C. for 2 hours) produced from a zirconia disc (manufactured by Kuraray Noritake Dental Inc. under the trade name "Noriand 2.5 cm in length) separately prepared was sandblasted using a 50-micron alumina abrasive (manufactured by J. Morita Corp.). Then, a dental cement composition obtained by mixing a dental cement comprising a first part and a second part was mounded. With the center of the circular hole being aligned with the center of the cylindrical stainless steel rod, the end surface with the dental cement composition mounded thereon was placed on and pressed against the circular hole in such a manner that the cylindrical stainless steel rod stands perpendicular to the zirconia surface. After the rod stood, the excess dental cement composition around the cylindrical stainless steel rod was removed with an instrument. Then, two points at the interface between the bottom surface of the stainless steel rod and the zirconia surface were each irradiated with light for 10 seconds using a dental LED photoirradiator (manufactured by J. Morita Corp. under the trade name "PenCure 2000"). The sample was left to stand at room temperature for 30 minutes, followed by immersion in distilled water to prepare an adhesion test sample. There were produced 20 such adhesion test samples. All samples in water were left to stand for 24 hours in a thermostatic chamber maintained at 37° C. To evaluate initial bond strength, 10 out of the 20 samples were measured for tensile bond strength immediately after left to stand for 24 hours. To evaluate bond durability, the remaining 10 samples were further subjected to 100,000 cycles of thermal cycling, one cycle of which consists of immersion in 4° C. cold water and 60° C. hot water for 1 minute each, and then measured for tensile bond strength.

The adhesion test samples were each measured for tensile bond strength using a universal testing machine (manufactured by Shimadzu Corporation) with a crosshead speed set at 2 mm/min, and the mean value was calculated as the tensile bond strength of the sample.

| | Components (parts by mass) | | Ex. 2-1 | Ex. 2-2 | Ex. 2-3 | Ex. 2-4 | Ex. 2-5 | Ex. 2-6 | Ex. 2-7 | Ex. 2-8 | Ex. 2-9 | Ex. 2-10 | Comp. Ex. 2-1 |
|---|---|---|---|---|---|---|---|---|---|---|---|---|---|
| First part | Dihydrogen phosphate monoester group-containing polymerizable monomer (A) | MDP | 20 | 20 | 20 | 20 | 10 | 40 | 20 | | 20 | 20 | 20 |
| | | MOP | | | | | | | | 20 | | | |
| | Dihydrogen phosphate monoester group-containing compound (B) | HDP | 0.05 | 0.1 | 0.5 | 0.8 | 0.01 | 0.2 | 0.05 | | 0.05 | 0.05 | |
| | | HOP | | | | | | | | 0.05 | | | |
| | Content of (B) relative to 100 parts by mass of (A) (parts by mass) | | 0.25 | 0.50 | 2.50 | 4.00 | 0.10 | 0.50 | 0.25 | 0.25 | 0.25 | 0.25 | 0.00 |
| | Polymerizable monomer (C) | Hydrophobic polymerizable monomer (C-1) having no acidic group | Bis-GMA | 40 | 40 | 40 | 40 | 40 | 40 | 30 | 40 | 40 | 40 | 40 |
| | | | D2.6E | 25 | 25 | 25 | 25 | 25 | 25 | 15 | 25 | 25 | 25 | 25 |
| | | | 3G | 15 | 15 | 15 | 15 | 15 | 15 | 10 | 15 | 15 | 15 | 15 |
| | | | MAEA | | | | | | | 10 | | | | |
| | | Hydrophilic polymerizable monomer (C.2) having no acidic group | HEMA | | | | | | | 10 | | | | |
| | | | DEAA | | | | | | | | 5 | | | |
| | Polymerization initiator (D) | Photopolymerization initiator (D-1) | CQ | 0.1 | 0.1 | 0.1 | 0.1 | 0.1 | 0.1 | 0.1 | 0.1 | | | 0.1 |
| | | Chemical polymerization initiator (D-2) | BPB | 0.5 | 0.5 | 0.5 | 0.5 | 0.5 | 0.5 | 0.5 | 0.5 | | | 0.5 |
| | | | BPO | | | | | | | | | 3 | | |
| | | | KPS | | | | | | | | | | 2 | |
| | Polymerization inhibitor | | BHT | 0.05 | 0.05 | 0.05 | 0.05 | 0.05 | 0.05 | 0.05 | 0.05 | 0.05 | 0.05 | 0.05 |
| | Filler (F) | | Inorganic filler 1 | 15 | 15 | 15 | 15 | 15 | 15 | 15 | 15 | 15 | 15 | 15 |
| | | | Inorganic filler 3 | 215 | 215 | 215 | 215 | 215 | 215 | 215 | 215 | 215 | 215 | 215 |
| Second part | Polymerizable monomer (C) | Hydrophobic polymerizable monomer (C-1) having no acidic group | D2.6E | 80 | 80 | 80 | 80 | 80 | 80 | 80 | 80 | 80 | 80 | 80 |
| | | | 3G | 20 | 20 | 20 | 20 | 20 | 20 | 20 | 20 | 20 | 20 | 20 |
| | Polymerization accelerator (E) | | DABE | 0.1 | 0.1 | 0.1 | 0.1 | 0.1 | 0.1 | 0.1 | 0.1 | 0.1 | 0.1 | 0.1 |
| | | | DEPT | 0.5 | 0.5 | 0.5 | 0.5 | 0.5 | 0.5 | 0.5 | 0.5 | 0.5 | 0.5 | 0.5 |
| | | | TPSS | 3 | 3 | 3 | 3 | 3 | 3 | 3 | 3 | 3 | 3 | 3 |
| | Polymerization inhibitor | | BHT | 0.05 | 0.05 | 0.05 | 0.05 | 0.05 | 0.05 | 0.05 | 0.05 | 0.05 | 0.05 | 0.05 |
| | Filler (F) | | Inorganic filler 2 | 10 | 10 | 10 | 10 | 10 | 10 | 10 | 10 | 10 | 10 | 10 |
| | | | Inorganic filler 4 | 220 | 220 | 220 | 220 | 220 | 220 | 220 | 220 | 220 | 220 | 220 |
| Initial bond strength | Tensile bond strength after being left for 24 hours (MPa) | | | 35 | 34 | 32 | 31 | 32 | 31 | 32 | 31 | 31 | 31 | 33 |
| Bond durability | Tensile bond strength after thermal cycling (MPa) | | | 30 | 29 | 27 | 26 | 27 | 26 | 26 | 25 | 27 | 27 | 19 |

As shown in Table 2, the dental cements according to the present invention (Examples 2-1 to 2-10) exhibited a tensile bond strength of 30 MPa or more as initial bond strength and a bond durability of 25 MPa or more as bond durability for sandblasted zirconia. In contrast, while having an initial bond strength of 30 MPa or more for zirconia, the dental cement (Comparative Examples 2-1) that did not contain the dihydrogen phosphate monoester group-containing monomer (B) had a bond durability of less than 20 MPa for zirconia.

INDUSTRIAL APPLICABILITY

A dental adhesive composition according to the present invention is suitably used as a dental primer, a dental bonding material, a self-adhesive dental composite resin, or a dental cement in the field of dentistry.

The invention claimed is:

1. A dental adhesive composition, comprising:
  (A) a dihydrogen phosphate monoester group-containing polymerizable monomer of formula (1):

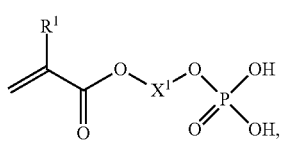

(1)

$R^1$ being H or a methyl group, and $X^1$ being an optionally substituted, linear or branched hydrocarbon group having 8 to 16 carbon atoms; and
  (B) a dihydrogen phosphate monoester group-containing compound of formula (2):

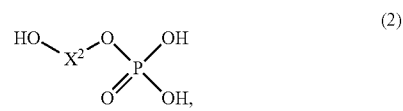

(2)

being an optionally substituted, linear or branched hydrocarbon group having 8 to 16 carbon atoms,
  wherein the hydrocarbon group of $X^1$ and/or $X^2$ optionally has a hydrocarbon chain comprising an —O—, —S—, and/or a phenylene group, and
  wherein the dihydrogen phosphate monoester group-containing compound (B) is present in a range of from 0.05 to 5.0 parts by mass, relative to 100 parts by mass of the dihydrogen phosphate monoester group-containing polymerizable monomer (A).

2. The dental adhesive composition of claim 1, further comprising:
  (C) a polymerizable monomer that is copolymerizable with the dihydrogen phosphate monoester group-containing polymerizable monomer (A).

3. The dental adhesive composition of claim 1, further comprising:
(D) a polymerization initiator.

4. The dental adhesive composition of claim 1, wherein $X^1$ and $X^2$ are the same.

5. The dental adhesive composition of claim 1, comprising the dihydrogen phosphate monoester group-containing compound (B) in a range of from 0.2 to 1.0 parts by mass, relative to 100 parts by mass of the dihydrogen phosphate monoester group-containing polymerizable monomer (A).

6. The dental adhesive composition of claim 1, wherein $X^1$ and $X^2$ are each independently an unsubstituted, linear alkylene group having 8 to 16 carbon atoms.

7. The dental adhesive composition of claim 1, further comprising:
(C) a polymerizable monomer that is copolymerizable with the dihydrogen phosphate monoester group-containing polymerizable monomer (A),
wherein the polymerizable monomer (C) comprises a hydrophobic polymerizable monomer (C-1) having no acidic group.

8. The dental adhesive composition of claim 1, further comprising:
(C) a polymerizable monomer that is copolymerizable with the dihydrogen phosphate monoester group-containing polymerizable monomer (A),
wherein the dihydrogen phosphate monoester group-containing compound (B) is present in a range of from 0.2 to 1.0 parts by mass, relative to 100 parts by mass of the dihydrogen phosphate monoester group-containing polymerizable monomer (A).

9. The dental adhesive composition of claim 1, further comprising:
(D) a polymerization initiator,
wherein the dihydrogen phosphate monoester group-containing compound (B) is present in a range of from 0.2 to 1.0 parts by mass, relative to 100 parts by mass of the dihydrogen phosphate monoester group-containing polymerizable monomer (A).

10. The dental adhesive composition of claim 1, comprising the dihydrogen phosphate monoester group-containing compound (B) in a range of from 0.2 to 1.0 parts by mass, relative to 100 parts by mass of the dihydrogen phosphate monoester group-containing polymerizable monomer (A),
wherein $X^1$ and $X^2$ are the same.

11. The dental adhesive composition of claim 1, further comprising:
(C) a polymerizable monomer that is copolymerizable with the dihydrogen phosphate monoester group-containing polymerizable monomer (A); and
(D) a polymerization initiator,
wherein the dihydrogen phosphate monoester group-containing compound (B) is present in a range of from 0.2 to 1.0 parts by mass, relative to 100 parts by mass of the dihydrogen phosphate monoester group-containing polymerizable monomer (A).

12. The dental adhesive composition of claim 1, further comprising:
(C) a polymerizable monomer that is copolymerizable with the dihydrogen phosphate monoester group-containing polymerizable monomer (A); and
(D) a polymerization initiator,
wherein the dihydrogen phosphate monoester group-containing compound (B) is present in a range of from 0.2 to 1.0 parts by mass, relative to 100 parts by mass of the dihydrogen phosphate monoester group-containing polymerizable monomer (A), and
wherein $X^1$ and $X^2$ are the same.

13. The dental adhesive composition of claim 1, further comprising:
(C) a polymerizable monomer that is copolymerizable with the dihydrogen phosphate monoester group-containing polymerizable monomer (A),
wherein the dihydrogen phosphate monoester group-containing compound (B) is present in a range of from 0.2 to 1.0 parts by mass, relative to 100 parts by mass of the dihydrogen phosphate monoester group-containing polymerizable monomer (A), and
wherein the polymerizable monomer (C) comprises a hydrophobic polymerizable monomer (C-1) having no acidic group.

14. The dental adhesive composition of claim 1, further comprising:
(C) a polymerizable monomer that is copolymerizable with the dihydrogen phosphate monoester group-containing polymerizable monomer (A),
wherein the dihydrogen phosphate monoester group-containing compound (B) is present in a range of from 0.2 to 1.0 parts by mass, relative to 100 parts by mass of the dihydrogen phosphate monoester group-containing polymerizable monomer (A), and
wherein $X^1$ and $X^2$ are each independently an unsubstituted, linear alkylene group having 8 to 16 carbon atoms.

15. The dental adhesive composition of claim 1, further comprising:
(C) a polymerizable monomer that is copolymerizable with the dihydrogen phosphate monoester group-containing polymerizable monomer (A),
wherein the dihydrogen phosphate monoester group-containing compound (B) is present in a range of from 0.2 to 1.0 parts by mass, relative to 100 parts by mass of the dihydrogen phosphate monoester group-containing polymerizable monomer (A),
wherein the polymerizable monomer (C) comprises a hydrophobic polymerizable monomer (C-1) having no acidic group, and
wherein $X^1$ and $X^2$ are each independently an unsubstituted, linear alkylene group having 8 to 16 carbon atoms.

16. The dental adhesive composition of claim 1, further comprising:
(C) a polymerizable monomer that is copolymerizable with the dihydrogen phosphate monoester group-containing polymerizable monomer (A),
wherein the dihydrogen phosphate monoester group-containing compound (B) is present in a range of from 0.2 to 1.0 parts by mass, relative to 100 parts by mass of the dihydrogen phosphate monoester group-containing polymerizable monomer (A),
wherein the polymerizable monomer (C) comprises a hydrophobic polymerizable monomer (C-1) having no acidic group, and
wherein $X^1$ and $X^2$ are the same.

17. The dental adhesive composition of claim 1, further comprising:
(C) a polymerizable monomer that is copolymerizable with the dihydrogen phosphate monoester group-containing polymerizable monomer (A),
wherein the dihydrogen phosphate monoester group-containing compound (B) is present in a range of from 0.2 to 1.0 parts by mass, relative to 100 parts by mass of the dihydrogen phosphate monoester group-containing polymerizable monomer (A), and wherein $X^1$ and $X^2$ are an identical unsubstituted, linear alkylene group having 8 to 16 carbon atoms.

18. The dental adhesive composition of claim 1, further comprising:
(C) a polymerizable monomer that is copolymerizable with the dihydrogen phosphate monoester group-containing polymerizable monomer (A),
wherein the dihydrogen phosphate monoester group-containing compound (B) is present in a range of from 0.2 to 1.0 parts by mass, relative to 100 parts by mass of the dihydrogen phosphate monoester group-containing polymerizable monomer (A),
wherein the polymerizable monomer (C) comprises a hydrophobic polymerizable monomer (C-1) having no acidic group, and
wherein $X^1$ and $X^2$ are an identical unsubstituted, linear alkylene group having 8 to 16 carbon atoms.

19. The dental adhesive composition of claim 1, further comprising:
(C) a polymerizable monomer that is copolymerizable with the dihydrogen phosphate monoester group-containing polymerizable monomer (A); and
(D) a polymerization initiator,
wherein the dihydrogen phosphate monoester group-containing compound (B) is present in a range of from 0.2 to 1.0 parts by mass, relative to 100 parts by mass of the dihydrogen phosphate monoester group-containing polymerizable monomer (A), and
wherein the polymerizable monomer (C) comprises a hydrophobic polymerizable monomer (C-1) having no acidic group.

20. The dental adhesive composition of claim 1, further comprising:
(C) a polymerizable monomer that is copolymerizable with the dihydrogen phosphate monoester group-containing polymerizable monomer (A); and
(D) a polymerization initiator,
wherein the dihydrogen phosphate monoester group-containing compound (B) is present in a range of from 0.2 to 1.0 parts by mass, relative to 100 parts by mass of the dihydrogen phosphate monoester group-containing polymerizable monomer (A), and
wherein $X^1$ and $X^2$ are each independently an unsubstituted, linear alkylene group having 8 to 16 carbon atoms.

* * * * *